(12) United States Patent
Hill

(10) Patent No.: US 9,981,003 B2
(45) Date of Patent: May 29, 2018

(54) CXCR ANTAGONISTIC PEPTIDES AND USES THEREOF

(71) Applicant: STC.UNM, Albuquerque, NM (US)

(72) Inventor: Jeff Wade Hill, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days. days.

(21) Appl. No.: 15/038,557

(22) PCT Filed: Nov. 25, 2014

(86) PCT No.: PCT/US2014/067356
§ 371 (c)(1),
(2) Date: May 23, 2016

(87) PCT Pub. No.: WO2015/077763
PCT Pub. Date: May 28, 2015

(65) Prior Publication Data
US 2016/0296588 A1 Oct. 13, 2016

Related U.S. Application Data

(60) Provisional application No. 61/908,307, filed on Nov. 25, 2013.

(51) Int. Cl.
*A61K 38/06* (2006.01)
*C07K 5/097* (2006.01)
*C07K 14/715* (2006.01)
*A61K 45/06* (2006.01)
*A61K 38/00* (2006.01)

(52) U.S. Cl.
CPC .............. *A61K 38/06* (2013.01); *A61K 45/06* (2013.01); *C07K 5/0823* (2013.01); *C07K 14/7158* (2013.01); *A61K 38/00* (2013.01)

(58) Field of Classification Search
None
See application file for complete search history.

(56) References Cited

U.S. PATENT DOCUMENTS

| 2007/0160574 A1 | 7/2007 | Merzouk et al. |
| 2010/0055088 A1 | 3/2010 | Peled et al. |

FOREIGN PATENT DOCUMENTS

| WO | 9802452 A2 | 1/1998 |
| WO | 0153331 A2 | 7/2001 |

OTHER PUBLICATIONS

Lin et al. "New descriptors of amino acids and their application to peptide QSAR study," p e p t i d e s 2 9 (2 0 0 8) 1 7 98-180 5.*
Shibata et al. (Identification of N-acetyl Proline-Glycine-Proline (acPGP) in human serum of adults and newborns by liquid chromatography—tandem mass spectrometry, Clinica Chimica Acta 402 (2009) 124-128).*
Nair AB, Jacob S. "A simple practice guide for dose conversion between animals and human," J Basic Clin Pharma 2016;7:27-31 (Year: 2016).*
Perico N, et al. Delayed graft function in kidney transplantation. Lancet, 2004;364:1814-1827.
Ten Hoeve et al.; Proline-Glycine-Proline as a potential biomarker in chronic obstructive pulmonary disease and cystic fibrosis. TANAFFOS 2012, vol. 11, No. 2, pp. 12-15.
Weathington et al.; A novel peptie CXCR ligand derived from extracellular matrix degradation during airway inflammation. Nature 2006, vol. 12, No. 3, pp. 317-323.
Kim et al.; Activation of CXCR2 by extracellular matrix degradation product acetylated Pro-Gly-Pro has therapeutic effects against sepsis. American Journal of Respiraatory and Critical Care Medicine 2011, vol. 184, No. 2. pp. 243-251.

* cited by examiner

*Primary Examiner* — Christina Bradley
(74) *Attorney, Agent, or Firm* — Henry D. Coleman; R. Neil Sudol

(57) ABSTRACT

The present invention provides a novel class of medicament based on CXCR antagonistic peptides. Among other things, the present invention provides peptides, compositions and methods for treating diseases, disorders and conditions in which a CXCR mediated pathway is implicated. Compositions and methods for effective treatment of inflammation, stroke, traumatic brain injury, pancreatic cancer, and others are provided.

7 Claims, 16 Drawing Sheets

CXCR ANTAGONISTIC PEPTIDES AND USES THEREOF

RELATED APPLICATIONS

This application is a U.S. national phase application based upon International Patent Application No. PCT/US2014/067356 filed on Nov. 25, 2014, which claims priority to U.S. Provisional Application Ser. No. 61/908,307 filed Nov. 25, 2013, the disclosure of which the two applications is hereby incorporated by reference.

BACKGROUND

CXC chemokine receptors are a subfamily of chemokine receptors that specifically bind and respond to cytokines of the CXC chemokine family. There are currently seven known CXC chemokine receptors in mammals, named CXCR1 through CXCR7. CXC receptors have been implicated in various inflammatory, autoimmune and other diseases, disorders or conditions.

Inflammation-related diseases, disorders or conditions include a variety of specific pathologies affecting millions of people. While several therapies have been developed, such as certain non-steroidal anti-inflammatory compounds for use in the treatment of rheumatoid arthritis, there is still a large unmet need for better and more efficacious therapies.

SUMMARY OF THE INVENTION

The present invention provides a novel class of medicament based on CXCR antagonistic peptides. Among other things, the present invention provides peptides, compositions and methods for treating diseases, disorders and conditions in which a CXCR mediated pathway is implicated. Thus, the present invention is particularly useful for effective treatment of inflammation, stroke, traumatic brain injury, pancreatic cancer, neurodegenerative diseases, to name but a few.

In one aspect, the present invention provides a peptide of less than 6 amino acids comprising the amino acid sequence proline-glycine-X (PGX) for use as a medicament, wherein X is any amino acid.

In another aspect, the present invention provides a peptide of less than 6 amino acids comprising the amino acid sequence proline-glycine-X (PGX) for use in the treatment of inflammation, wherein X is any amino acid. In some embodiments, the inflammation is associated with arthritis (including rheumatoid arthritis and juvenile rheumatoid arthritis); vasculitis; multiple sclerosis; autoimmune thyroiditis; inflammatory bowel disease (IBD); Crohn's disease; inflammatory conditions of the nervous system (e.g., Alzheimer's disease), liver (e.g., hepatitis), kidney (e.g., nephritis) and pancreas (e.g., pancreatitis); cardiovascular disorders (e.g., pulmonary fibrosis, idiopathic pulmonary fibrosis, reperfusion injury, acute vaso-occlusive crisis in sickle cell anemia); respiratory disorders, e.g., COPD (e.g., cystic fibrosis); and infectious disease (e.g., acute endocarditis, pericarditis); adult respiratory distress syndrome (ARDS); Chronic Obstructive Pulmonary disease (COPD); tumors or cancers (e.g., soft tissue or solid tumors), such as melanoma or prostate cancer; or transplant rejection (e.g. destruction of pancreatic islet cells in islet cell transplantation, delayed graft failure in kidney or other organ transplantation); acute and chronic graft versus host disease. In some embodiments, the inflammation is associated with an acute inflammatory condition. In some embodiments, the inflammation is associated with a chronic inflammatory condition. In some embodiments, the inflammation is neuroinflammation associated with stroke.

In still another aspect, the present invention provides a peptide of less than 6 amino acids comprising the amino acid sequence proline-glycine-X (PGX) for use in the treatment of stroke, wherein X is any amino acid.

In another aspect, the present invention provides a peptide of less than 6 amino acids comprising the amino acid sequence proline-glycine-X (PGX) for use in the treatment of traumatic brain injury, wherein X is any amino acid.

In yet another aspect, the present invention provides a peptide of less than 6 amino acids comprising the amino acid sequence proline-glycine-X (PGX) for use in the treatment of pancreatic cancer, wherein X is any amino acid.

In further aspect, the present invention provides a peptide of less than 6 amino acids comprising the amino acid sequence proline-glycine-X (PGX) for use in the treatment or prevention of neuronal death, wherein X is any amino acid. In some embodiments, neuronal death is associated with a neurodegenerative disease. In some embodiments, the neurodegenerative disease is selected from the group consisting of amyotrophic lateral sclerosis (ALS), Huntington's disease, Alzheimer's disease, Parkinson's disease, multiple sclerosis, vascular cognitive impairment (VCI), and combinations thereof.

In another aspect, the present invention provides methods of treating inflammation, comprising administering to a subject in need thereof a peptide of less than 6 amino acids containing the amino acid sequence proline-glycine-X (PGX), wherein X is any amino acid, or a composition containing such peptide.

In some embodiments, the inflammation is associated with arthritis (including rheumatoid arthritis and juvenile rheumatoid arthritis); vasculitis; multiple sclerosis; autoimmune thyroiditis; inflammatory bowel disease (IBD); Crohn's disease; inflammatory conditions of, the nervous system (e.g., Alzheimer's disease), liver (e.g., hepatitis), kidney (e.g., nephritis) and pancreas (e.g., pancreatitis); cardiovascular disorders (pulmonary fibrosis, idiopathic pulmonary fibrosis, reperfusion injury, acute vaso-occlusive crisis in sickle cell anemia); respiratory disorders, e.g., COPD (e.g., cystic fibrosis); and infectious disease (e.g., acute endocarditis, pericarditis); adult respiratory distress syndrome (ARDS); Chronic Obstructive Pulmonary disease (COPD); tumors or cancers (e.g., soft tissue or solid tumors), such as melanoma or prostate cancer; and/or transplant rejection (e.g. destruction of pancreatic islet cells in islet cell transplantation, delayed graft failure in kidney or other organ transplantation); acute and chronic graft versus host disease. In some embodiments, the inflammation is associated with an acute inflammatory condition. In some embodiments, the inflammation is associated with a chronic inflammatory condition. In some embodiments, the inflammation is neuroinflammation associated with stroke.

In another aspect, the present invention provides methods of treating stroke, comprising administering to a subject in need of treatment a peptide of less than 6 amino acids containing the amino acid sequence PGX, wherein X is any amino acid, or a composition comprising such peptide.

In another aspect, the present invention provides methods of treating brain injury (e.g., traumatic brain injury), comprising administering to a subject in need of treatment a peptide of less than 6 amino acids containing the amino acid sequence PGX, wherein X is any amino acid, or a composition comprising such peptide.

In another aspect, the present invention provides methods of treating pancreatic cancer, comprising administering to a subject in need of treatment a peptide of less than 6 amino acids containing the amino acid sequence PGX, wherein X is any amino acid, or a composition comprising such peptide.

In further aspect, the present invention provides methods of treating or preventing neuronal death, comprising administering to a subject in need of treatment a peptide of less than 6 amino acids containing the amino acid sequence of PGX, wherein X is any amino acid, or a composition comprising such peptide. In some embodiments, the neuronal death is associated with a neurodegenerative disease. In some embodiments, the neurodegenerative disease is selected from the group consisting of amyotrophic lateral sclerosis (ALS), Huntington's disease, Alzheimer's disease, Parkinson's disease, multiple sclerosis, vascular cognitive impairment (VCI), and combinations thereof.

In another aspect, the present invention provides methods of inhibiting a CXC receptor activity in a cell, comprising administering to a cell peptides of less than 6 amino acids containing the amino acid sequence proline-glycine-X (PGX), wherein X is any amino acid. In some embodiments, the cell is a mammalian cell. In some embodiments, the cell is a human cell. In some embodiments, the cell is a cultured cell. In some embodiments, the cell is in a living organism. In some embodiments, the CXC receptor is selected from CXCR1, CXCR2, CXCR3, CXCR4, CXCR5, CXCR6, and/or CXCR7. In some embodiments, the CXC receptor is CXCR1 or CXCR2.

In still another aspect, the present invention provides a method of inhibiting a CXC receptor activity in a subject, comprising administering to a subject in need thereof a peptide of less than 6 amino acids containing the amino acid sequence proline-glycine-X (PGX), wherein X is any amino acid.

In various embodiments, a suitable peptide contains the amino acid sequence proline-glycine-X (PGX), wherein X is any amino acid except proline. In various embodiments, a suitable peptide contains the amino acid sequence proline-glycine-X (PGX), wherein X is glycine. In some embodiments, the amino acid sequence proline-glycine-X (PGX) is at the N-terminus. In some embodiments, a suitable peptide is acetylated or methylated at the N-terminus. In some embodiments, a suitable peptide has less than 5 amino acids. In some embodiments, a suitable peptide has less than 4 amino acids. In some embodiments, a suitable peptide is the N-acetylated tripeptide ac-PGG. In some embodiments, a suitable peptide is PEGylated.

In some embodiments, a suitable peptide contains a plurality of PGX repeats. In some embodiments, a suitable peptide contains 2-50, 2-40, 2-30, 2-20, 2-15, 2-10, 2-8, 2-6, or 2-5 PGX repeats. In some embodiments, a suitable peptide contains more than 2, 3, 4, 5, 10, 15, 20, 25, 30, 35, 40, 45 or 50 PGX repeats. In some embodiments, a suitable peptide contains PGX repeats wherein the PGX repeats are tandem repeats. In some embodiments, a suitable peptide contains PGX repeats wherein the PGX repeats are interrupted by non-PGX sequences. In some embodiments, a suitable peptide contains PGX repeats wherein the PGX repeats are linear and/or branched.

In various embodiments, a suitable peptide is administered intravenously, subcutaneously, orally, transdermally, intramuscularly, intraperitoneally, and/or by aerosol inhalation.

In still another aspect, the present invention provides pharmaceutical compositions comprising a therapeutically effective amount of a peptide (e.g., of less than 6, 5, or 4 amino acids) and containing a sequence of PGX, wherein X is any amino acid except proline and a pharmaceutically acceptable carrier or excipient. In some embodiments, X is any amino acid except proline. In some embodiments, X is glycine. In some embodiments, a pharmaceutical composition according to the invention contains a peptide that is PEGylated. In some embodiments, a pharmaceutical composition according to the invention contains a peptide wherein the sequence of proline-glycine-X (PGX) is at the N-terminus. In some embodiments, a pharmaceutical composition according to the invention contains a peptide acetylated or methylated at the N-terminus. In some embodiments, a pharmaceutical composition according to the invention contains an N-acetylated tripeptide ac-PGG. In some embodiments, a pharmaceutical composition according to the invention contains a peptide with a plurality of PGX repeats. In some embodiments, a pharmaceutical composition according to the invention contains a peptide with 2-50, 2-40, 2-30, 2-20, 2-15, 2-10, 2-8, 2-6, or 2-5 PGX repeats. In some embodiments, a pharmaceutical composition according to the invention contains a peptide with more than 2, 3, 4, 5, 10, 15, 20, 25, 30, 35, 40, 45 or 50 PGX repeats. In some embodiments, a pharmaceutical composition according to the invention contains a peptide with PGX repeats that are tandem repeats. In some embodiments, a pharmaceutical composition according to the invention contains a peptide with PGX repeats wherein the PGX repeats are interrupted by non-PGX sequences. In some embodiments, a pharmaceutical composition according to the invention contains a peptide with PGX repeats wherein the PGX repeats are linear and/or branched.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The drawings are for illustration purposes only, not for limitation.

DEFINITIONS

Figure 1A:
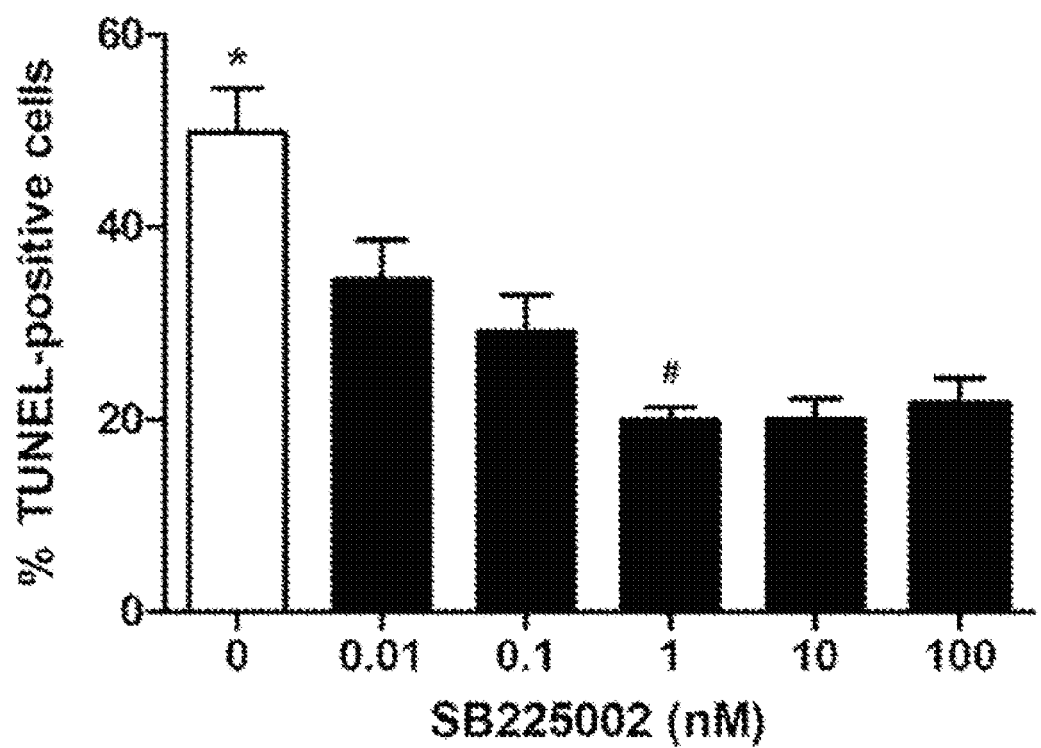
FIG. 1 depicts exemplary graphs showing the effects of pretreatment of neurons with several doses of SB225002, anti-CXCR2 ligand binding domain antibody, or ac-PGG on ac-PGP-induced apoptosis as measured via a TUNEL stain. A. Cells pretreated with all doses of SB225002 were significantly less apoptotic than cells treated with ac-PGP only (*). Cells pretreated with 1 nM SB225002 were significantly less apoptotic than cells treated with 0.01 and 0.1 nM SB225002 (#). B. Cells pretreated with CXCR2 antibody at a 1:1000 (1e3) or greater dilution exhibited significantly less apoptosis than ac-PGP alone (*) while a 1e3 dilution produced significantly less apoptosis than a 1e2 dilution (#). C. Neurons pretreated with all doses of ac-PGG were significantly less apoptotic than ac-PGP treatment alone (*). Cells pretreated with 100 nM ac-PGG were significantly less apoptotic than cells pretreated with 0.01 nM ac-PGG (#).

In order for the present invention to be more readily understood, certain terms are first defined below. Additional definitions for the following terms and other terms are set forth throughout the specification.

Agonist: As used herein, the term "agonist" refers to any molecule that has a positive impact in a function of a protein of interest. In some embodiments, an agonist directly or indirectly enhances, strengthens, and/or increases an activity of a protein of interest. In particular embodiments, an agonist directly interacts with the protein of interest. Agonists can be, e.g., proteins, chemical compounds, small molecules, nucleic acids, antibodies, drugs, ligands, or other agents.

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Examples of unconventional or un-natural amino acids include, but are not limited to, citrulline, ornithine, norleucine, norvaline, 4-(E)-butenyl-4(R)-methyl-N-methylthreonine (MeBmt), N-methyl-leucine (MeLeu), aminoisobutyric acid, statin, and N-methyl-alanine (MeAla). Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antagonist: As used herein, the term "antagonist" refers to any molecule that has a negative impact in a function of a protein of interest. In some embodiments, an antagonist directly or indirectly reduces, inhibits, or down-regulates an activity of a protein of interest. In particular embodiments, an antagonist directly interacts with the protein of interest. Antagonists can be, e.g., proteins, chemical compounds, small molecules, nucleic acids, antibodies, drugs, ligands, or other agents.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Functional equivalent or derivative: As used herein, the term "functional equivalent" or "functional derivative" denotes a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Prevent: As used herein, the term "prevent" or "prevention", when used in connection with the occurrence of a disease, disorder, and/or condition, refers to reducing the risk of developing the disease, disorder and/or condition. See the definition of "risk."

Polypeptide: The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified. The terms "peptide" and "polypeptide" are used interchangeably herein.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., an inflammation-related disease, disorder, or condition). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., an inflammation-related disease, disorder, or condition). In some embodiments a reference sample or group of reference samples are from individuals comparable to a particular individual. In some embodiments, relative risk is 0, 1, 2, 3, 4, 5, 6, 7, 8, 9, 10, or more.

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In certain embodiments, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization).

Subject: As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, a novel class of medicaments based on CXCR antagonistic peptides. In particular, the present invention provides compositions and methods for treatment of CXCR related diseases, disorders and conditions.

Various aspects of the invention are described in detail in the following sections. The use of sections is not meant to limit the invention. Each section can apply to any aspect of the invention. In this application, the use of "or" means "and/or" unless stated otherwise.

CXC Receptors

Generally speaking, CXC receptors (CXCR) are chemokine receptors that bind and respond to cytokines of the CXC chemokine family. Typically, they are members of G protein-linked receptors, also known as seven transmembrane (7-TM) proteins, because they are characterized with spanning the cell membrane seven times. CXCRs according to the present invention include, but not limited to, CXCR1 through CXCR7 (i.e., CXCR1, CXCR2, CXCR3, CXCR4, CXCR5, CXCR6 and CXCR7).

CXCR1 and CXCR2 are closely related receptors that recognize CXC chemokines that possess an E-L-R amino acid motif immediately adjacent to their CXC motif. CXCL8 (otherwise known as interleukin-8) and CXCL6 can both bind CXCR1 in humans, while all other ELR-positive chemokines, such as CXCL1 to CXCL7 bind only CXCR2. They are both expressed on the surface of neutrophils in mammals.

CXCR3 is expressed predominantly on T lymphocytes, and also on other lymphocytes (some B cells and NK cells) and is highly induced following cell activation. There are two isoforms, CXCR3-A and CXCR3-B. It has three highly related ligands in mammals, CXCL9, CXCL10 and CXCL11.

CXCR4 (also known as fusin) is the receptor for a chemokine known as CXCL12 (or SDF-1) and, as with CCR5, is utilized by HIV-1 to gain entry into target cells. This receptor has a wide cellular distribution, with expression on most immature and mature hematopoietic cell types (e.g., neutrophils, monocytes, T and B cells, dendritic cells, Langerhans cells and macrophages). In addition, CXCR4 can also be found on vascular endothelial cells and neuronal/nerve cells.

CXCR5 is selectively expressed on B cells and is involved in lymphocyte homing and the development of normal lymphoid tissue. Its principle ligand is CXCL13 (or BLC).

CXCR6 was formerly called three different names (STRL33, BONZO, and TYMSTR) before being assigned CXCR6 based on its chromosomal location (within the chemokine receptor cluster on human chromosome 3p21) and its similarity to other chemokine receptors in its gene sequence. CXCR6 binds the ligand CXCL16. However, CXCR6 is more closely related in structure to CC chemokine receptors than to other CXC chemokine receptors.

CXCR7 was originally called RDC-1 (an orphan receptor) but has since been shown to cause chemotaxis in T lymphocytes in response to CXCL12 (the ligand for CXCR4) prompting the renaming of this molecule as CXCR7. There is no information publicly available to confirm whether this designation has been accepted by the IUIS/WHO Subcommittee on Chemokine Nomenclature at this time. This receptor has also been identified on memory B cells.

CXCR Antagonistic Peptides

As used herein, the terms "peptide" and "polypeptide" include linear, branched and cyclic peptides. As used herein, a CXC receptor (CXCR) refers to any chemokine receptor that specifically binds and responds to a cytokine of the CXC chemokine family. A CXCR includes, but is not limited to, CXCR1, CXXR2, CXCR2, CXCR3, CXCR4, CXCR5, CXCR5, CXCR6, and/or CXCR7. As used herein, the term "CXCR antagonistic peptide" refers to any peptide that has a negative impact in a function of a CXCR. In some embodiments, a CXCR antagonistic peptide directly or indirectly reduces, inhibits, or down-regulates the activity of a CXCR. In some embodiments, provided peptides are isolated peptides.

According to the present invention, a CXCR antagonistic peptide contains the amino acid sequence proline-glycine-X (PGX, or Pro-Gly-Xaa), wherein X is any amino acid. In some embodiments, X is selected from Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In some embodiments, X is not proline. In some embodiments, X is glycine.

According to various embodiments, amino acids may be from natural or non-natural sources, provided that at least one amino group and at least one carboxyl group are present in the molecule. In some embodiments, provided peptides comprise naturally occurring amino acids. In some embodiments, provided peptides comprise one or more synthetic or un-naturally occurring amino acids (e.g., α,α-disubstituted amino acids, N-alkyl amino acids). In some embodiments, provided peptides comprise one or more D-amino acid. In some embodiments, provided peptides comprise one or more L-amino acid. Provided peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications, for example, of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Exemplary modifications are further described below.

In some embodiments, provided peptides comprise one or more residues other than common amino acids. According to various embodiments, residues other than common amino acids that may be present in a provided peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

In some embodiments, the present invention provides polypeptides comprising an amino acid sequence of between 3 and 60 amino acids in length (e.g., between 3-55, 3-50, 3-45, 3-40, 3-35, 3-30, 3-25, 3-20, 3-15, 3-10, or 3-6 amino acids in length). In some embodiments, provided peptides are between 3 and 15 amino acids in length (e.g., 3, 4, 5, 6, 7, 8, 9, 10, 11, 12, 13, 14, or 15 amino acids in length). In some embodiments, provided peptides are less than 15 amino acids in length (e.g., less than 14, 13, 12, 11, 10, 9, 8, 7, 6, 5, or 4 amino acids in length). In some embodiments, provided peptides are less than 6 amino acids in length.

In some embodiments, the sequence Pro-Gly-Xaa is located at the N-terminus of the peptide. In some embodiments, the sequence Pro-Gly-Xaa is located at the C-terminus of the peptide. In some embodiments, the sequence Pro-Gly-Xaa is located internally.

In some embodiments, the sequence Pro-Gly-Xaa may appear as repeats. For example, a peptide according to the present invention may contain 2-50, 2-40, 2-30, 2-20, 2-15, 2-10, 2-8, 2-6, or 2-5 PGX repeats. In some embodiments, a peptide according to the present invention may contain more than 2, 3, 4, 5, 6, 7, 8, 9, 10, 11, 12, 13, 14, 15, 20, 25, 30, 35, 40, 45 or 50 PGX repeats. The PGX repeats may appear as tandem repeats (i.e., consecutive repeats), may be interrupted by non-PGX sequences (e.g., by one or more amino acids that do not appear as PGX), or both. the PGX repeats can also be linear, branched or both. In some embodiments, Xaa comprises the same amino acid each repeat. In some embodiments, Xaa comprises a different amino acid (and/or a different form of a particular amino acid) in each repeat. In some embodiments, Xaa comprises a different amino acid (and/or a different form of a particular amino acid) in two or more repeats.

Peptide Modifications

In some embodiments, amino acids at one or more positions in a provided peptide comprise one or more modifications. In some embodiments, a particular modification may impart one or more improved characteristics to a peptide. For example, a modification may increase the potency and/or half-life of a peptide.

In some embodiments, provided peptides are modified at the N-terminus. For example, N-terminal acetylation, methylation, or alkoxycarbonylation. In some embodiments, a peptide according to the invention is N-acetylated PGX, wherein X is any amino acid. In some embodiments, X is not proline. In particular embodiments, a peptide according to the invention is N-acetylated PGG. In some embodiments, provided proteins are modified at the C-terminus. In some embodiments, provided peptides are modified at an amino acid position other than the N-terminal or C-terminal position.

Any of a variety of known modifications of amino acids may be implemented in the scope of the invention. For example, several known modifications compatible with various embodiments may be found and described at www.piercenet.com/previews/guides/custom-peptide-modifications, the disclosure of which is hereby incorporate by reference. In some embodiments, a modification comprises attachment of an acetyl group to a particular amino acid. In some embodiments, a modification is PEGylation comprising the addition of at least one monomeric unit of polyethylene glycol (PEG):

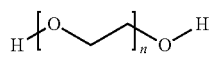

In some embodiments, provided peptides comprise two or more monomeric units of PEG (i.e. PEG oligomers or multimers).

In some embodiments, a modification comprises hydroxylation, oxidation, phosphorylation, adenylylation, glycation, glycosylation, and/or biotinylation of a particular amino acid.

In some embodiments, provided peptides are modified by the attachment of a alkyl group (e.g. methyl, ethyl) to one or more amino acids. In some embodiments, provided peptides are modified by the attachment of a alkyl group to one or more amino acids. In some embodiments, provided peptides are modified by the attachment of a glycosyl group to one or more amino acids. In some embodiments, provided peptides are modified by the attachment of a flavin and/or 4'-phosphopantetheinyl moiety to one or more amino acids.

In some embodiments, provided peptides are modified by citrullination, deamidation, ubiquitination, eliminylation, and/or carbamylation. In some embodiments, provided peptides are modified by the attachment of one or more myristate, lipoate, palmitate, and/or isoprenoid molecules.

In some embodiments, provided peptides are modified by pyroglutamate formation. In some embodiments, provided peptides are modified by S-glutathionylation. In some embodiments, provided peptides are modified by S-nitrosylation. In some embodiments, provided peptides are modified by succinylation. In some embodiments, provided peptides are modified by sulfation.

Cyclic Peptides

In some embodiments, provided peptide are cyclic peptides. As used herein, a cyclic peptide has an intramolecular covalent bond between two non-adjacent residues. The intramolecular bond may be a backbone to backbone, side-chain to backbone or side-chain to side-chain bond (i.e., terminal functional groups of a linear peptide and/or side-chain functional groups of a terminal or interior residue may be linked to achieve cyclization). Typical intramolecular bonds include disulfide, amide and thioether bonds. A variety of means for cyclizing polypeptides are well known in the art, as are many other modifications that can be made to such peptides. For a general discussion, see International Patent Publication Nos. WO 01/53331 and WO 98/02452, the contents of which are incorporated herein by reference. Such cyclic bonds and other modifications can also be applied to the cyclic peptides and derivative compounds of this invention.

As with provided linear or branched peptides, amino acids in provided cyclic peptides may comprise one or more modifications. In some embodiments, amino acids may be from natural or non-natural sources, provided that at least one amino group and at least one carboxyl group are present in the molecule; α- and β-amino acids are generally preferred. Cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Suitable derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. Alternatively, strong oxidizing agents such as I2 and K3Fe(CN)6 can be used to form disulfide linkages. Those of ordinary skill in the art will recognize that care must be taken not to oxidize the sensitive side chains of Met, Tyr, Trp or His. Within further embodiments, cyclization may be achieved by amide bond formation. For example, a peptide bond may be formed between terminal functional groups (i.e., the amino and carboxy termini of a linear peptide prior to cyclization). Alternatively, cyclization may be accomplished by linking one terminus and a residue side chain or using two side chains, with or without an N-terminal acetyl group and/or a C-terminal amide. Exemplary residues capable of forming a lactam bond include lysine, ornithine (Orn), α-amino adipic acid, m-aminomethylbenzoic acid, α,β-diaminopropionic acid, glutamate or aspartate. Methods for forming amide bonds are generally well known in the art. Within one such method, carbodiimide-mediated lactam formation can be accomplished by reaction of the carboxylic acid with DCC, DIC, ED AC or DCCI, resulting in the formation of an O-acylurea that can be reacted immediately with the free amino group to complete the cyclization. Alternatively, cyclization can be performed using the azide method, in which a reactive azide intermediate is generated from an alkyl ester via a hydrazide. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF.

Therapeutic Application

Various peptides described herein may be used to inhibit, reduce, decrease, or down-regulate a CXCR activity in a cell or a subject. For example, a peptide described herein may be used to inhibit, reduce, decrease, or down-regulate a CXCR activity and/or a CXCR mediated pathway in a mammalian cell (e.g., a human cell), such as in a cultured cell or a cell of a living organism. In some embodiments, peptides described herein can also be used to inhibit, reduce, decrease, or down-regulate a CXCR activity in a subject. In some embodiments, a peptide described herein inhibits, reduces, decreases, or down-regulates the activity of CXCR1, CXCR2, CXCR3, CXCR4, CXCR5, CXCR6, and/or CXCR7. In particular embodiments, a peptide described herein inhibits, reduces, decreases, or down-regulates the activity of CXCR1 and/or CXCR2.

In various embodiments, peptides described herein may be used to treat diseases, disorders and conditions in which a CXCR mediated pathway is implicated. In some embodiments, peptides described herein may be used to treat inflammation, stroke, traumatic brain injury, pancreatic cancer, to name but a few.

Exemplary diseases, disorders, or conditions that can be treated according to the present invention are provided below.

Inflammation

In some embodiments, provided peptides are used in the treatment of inflammation. For example, provided peptides can be used in the treatment of inflammation associated with arthritis (including rheumatoid arthritis, juvenile rheumatoid arthritis, osteoarthritis, psoriatic arthritis, lupus-associated arthritis or ankylosing spondylitis); scleroderma; systemic lupus erythematosis; HIV; Sjogren's syndrome; vasculitis; multiple sclerosis; autoimmune thyroiditis; asthma (e.g., allergic and non-allergic asthma); dermatitis (including atopic dermatitis and eczematous dermatitis); myasthenia gravis; inflammatory bowel disease (IBD); Crohn's disease; colitis; diabetes mellitus (type I); inflammatory conditions of, e.g., the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis); sarcoidosis; scleroderma; cirrhosis; eosinophilic esophagitis; cardiovascular disorders (e.g., cholesterol metabolic disorders, oxygen free radical injury, ischemia, pulmonary fibrosis, idiopathic pulmonary fibrosis, reperfusion injury, acute vaso-occlusive crisis in sickle cell anemia; disorders associated with wound healing; respiratory disorders, e.g., asthma, COPD (e.g., cystic fibrosis); acute inflammatory conditions (e.g., endotoxemia, sepsis and septicaemia, toxic shock syndrome and infectious disease (e.g., myocarditis, cardiomyopathy, acute endocarditis, pericarditis); Systemic Inflammatory Response Syndrome (SIRS)/sepsis; atopic disorders, e.g., urticaria, allergic rhinitis, rhinosinusitis (e.g., chronic allergic rhinosinusitis) allergic enterogastritis; adult respiratory distress syndrome (ARDS); systemic erythematosis (SLE); Airway hyperresponsiveness (AHR); bronchial hyperreactivity; Chronic Obstructive Pulmonary disease (COPD); Congestive Heart Failure (CHF); inflammatory bowel disease; inflammatory complications of diabetes mellitus; metabolic syndrome; end-stage renal disease (ESRD); muscle fatigue or inflammation and dermal conditions; inflammatory conditions caused by bacterial infection or viral infection (e.g. respiratory syncytial virus-induced airway hyperreactivity); tumors or cancers (e.g., soft tissue or solid tumors), such as leukemia (e.g., Hodgkin's lymphoma), glioblastoma, astrocytoma, lymphoma, melanoma or prostate cancer; or transplant rejection (e.g. destruction of pancreatic islet cells in islet cell transplantation, delayed graft failure in kidney or other organ transplantation); acute and chronic graft versus host disease.

Arthritis

In some embodiments, provided peptides are used in the treatment of arthritis (including rheumatoid arthritis, juvenile rheumatoid arthritis, osteoarthritis, psoriatic arthritis, lupus-associated arthritis or ankylosing spondylitis). Arthritis is a joint disorder that involves inflammation of one or more joints. There are over 100 different forms of arthritis. The most common form, osteoarthritis (degenerative joint disease), is a result of trauma to the joint, infection of the joint, or age. Other arthritis forms are rheumatoid arthritis, psoriatic arthritis, and related autoimmune diseases. Septic arthritis is caused by joint infection.

The major complaint by individuals who have arthritis is joint pain. Pain is often a constant and may be localized to the joint affected. The pain from arthritis is due to inflammation that occurs around the joint, damage to the joint from disease, daily wear and tear of joint, muscle strains caused by forceful movements against stiff painful joints and fatigue. Other common symptoms of arthritis include varied levels of swelling, joint stiffness and a constant ache around the joint(s).

Arthritis is the most common cause of disability in the USA. More than 20 million individuals with arthritis have severe limitations in function on a daily basis. Absenteeism and frequent visits to the physician are common in individuals who have arthritis. Arthritis makes it very difficult for individuals to be physically active and some become home bound. It is estimated that the total cost of arthritis cases is close to $100 billion of which nearly 50% is from lost earnings. Each year, arthritis results in nearly 1 million hospitalizations and close to 45 million outpatient visits to health care centers. Arthritis can make it very difficult for an individual to remain physically active, contributing to an increased risk of obesity, high cholesterol or vulnerability to heart disease. Individuals with arthritis are also at increased risk of depression, which may be related to fear of worsening symptoms. Other significant secondary changes that are common in patients with advanced arthritis are muscle weakness, loss of flexibility and decreased aerobic fitness, which can all occur in patients who have limited their physical activity.

Rheumatoid Arthritis

In some embodiments, provided peptides are used in the treatment of rheumatoid arthritis. Rheumatoid arthritis is a chronic inflammatory disorder that typically affects the small joints in the hands and feet. Unlike the wear-and-tear damage of osteoarthritis, rheumatoid arthritis affects the lining of the joints, causing a painful swelling that can eventually result in bone erosion and joint deformity.

Signs and symptoms of rheumatoid arthritis may include: tender, warm, swollen joints, morning stiffness that may last for hours, firm bumps of tissue under the skin on the arms (rheumatoid nodules), fatigue, fever and weight loss. Early rheumatoid arthritis tends to affect the smaller joints first, particularly the joints that attach the fingers to the hands and the toes to the feet. As the disease progresses, symptoms often spread to the knees, ankles, elbows, hips and shoulders. In most cases, symptoms occur in the same joints on both sides of the body. Rheumatoid arthritis signs and symptoms may vary in severity and may even come and go. Periods of increased disease activity, called flares, alternate with periods of relative remission, when the swelling and pain fade or disappear. Over time, rheumatoid arthritis can cause joints to deform and shift out of place.

Rheumatoid arthritis occurs when the immune system attacks the synovium, the lining of the membranes that surround joints. The resulting inflammation thickens the synovium, which can eventually destroy the cartilage and bone within the joint. The tendons and ligaments that hold the joint together weaken and stretch. Gradually, the joint loses its shape and alignment. Doctors don't know what starts this process, although a genetic component appears likely. While one's genes don't actually cause rheumatoid arthritis, they can make a person more susceptible to environmental factors, such as infection with certain viruses and bacteria, which may trigger the disease.

Juvenile Rheumatoid Arthritis

In some embodiments, provided peptides are used in the treatment of juvenile rheumatoid arthritis. Juvenile rheumatoid arthritis is the most common type of arthritis in children under the age of 16. Juvenile rheumatoid arthritis causes persistent joint pain, swelling and stiffness. In some cases, juvenile arthritis affects the entire body, causing swollen lymph nodes, rashes and fever. Some children may experience symptoms for only a few months, while others have symptoms for the rest of their lives.

Some types of juvenile rheumatoid arthritis can cause serious complications, such as growth problems and eye inflammation (uveitis). If eye inflammation is left untreated, it may result in cataracts, glaucoma and even blindness. Eye inflammation frequently occurs without symptoms, so it's important for children with juvenile rheumatoid arthritis to be examined regularly by an ophthalmologist. Growth problems associated with juvenile rheumatoid arthritis can also involve problems with bone development; some medications used to treat the disease, such as corticosteroids, can also inhibit growth.

Juvenile rheumatoid arthritis occurs when the body's immune system attacks its own cells and tissues. It's unknown why this happens, but both heredity and environment seem to play a role. Certain gene mutations may make a person more susceptible to environmental factors—such as viruses—that may trigger the disease.

Osteoarthritis

In some embodiments, provided peptides are used in the treatment of osteoarthritis. Osteoarthritis is one of the most common form of arthritis. It can affect both the larger and the smaller joints of the body, including the hands, wrists, feet, back, hip, and knee. The disease is essentially one acquired from daily wear and tear of the joint; however, osteoarthritis can also occur as a result of injury. Osteoarthritis begins in the cartilage and eventually causes the two opposing bones to erode into each other.

Initially, the condition starts with minor pain during activities, but soon the pain can be continuous and even occur while in a state of rest. The pain can be debilitating and prevent one from doing some activities. Other symptoms can include tenderness (joints may feel tender when light pressure is applied), stiffness (most noticeable after awakening or after a period of inactivity), loss of flexibility, a grating sensation and bone spurs (extra bits of bone that feel like hard lumps and can form around the affected joint).

Osteoarthritis typically affects the weight-bearing joints, such as the back, spine, and pelvis.

Unlike rheumatoid arthritis, osteoarthritis is most commonly a disease of the elderly. More than 30 percent of women have some degree of osteoarthritis by age 65. Osteoarthritis occurs when the cartilage that cushions the ends of bones in joints deteriorates over time. Cartilage is a firm, slippery tissue that permits nearly frictionless joint motion. In osteoarthritis, the slick surface of the cartilage becomes rough. Eventually, if the cartilage wears down completely, a patient may be left with bone rubbing on bone. Risk factors for osteoarthritis include prior joint trauma, obesity, and a sedentary lifestyle.

Psoriatic Arthritis

In some embodiments, provided peptides are used in the treatment of psoriatic arthritis. Psoriatic arthritis is a form of arthritis that affects some people who have psoriasis, a condition that features red patches of skin topped with silvery scales. Most people develop psoriasis first and are later diagnosed with psoriatic arthritis, but the joint problems can sometimes begin before skin lesions appear. Joint pain, stiffness and swelling are the main symptoms of psoriatic arthritis.

They can affect any part of the body, including fingertips and spine, and can range from relatively mild to severe. Psoriatic arthritis can cause a painful, sausage-like swelling of the fingers and toes. Patients may also develop swelling and deformities in the hands and feet before having significant joint symptoms. Psoriatic arthritis can also cause pain at the points where tendons and ligaments attach to the bones—especially at the back of the heel (Achilles tendinitis) or in the sole of the foot (plantar fasciitis). Some people develop a condition called spondylitis as a result of psoriatic arthritis. Spondylitis mainly causes inflammation of the joints between the vertebrae of the spine and in the joints between the spine and pelvis (sacroiliitis). A small percentage of people with psoriatic arthritis develop arthritis mutilans—a severe, painful and disabling form of the disease. Over time, arthritis mutilans destroys the small bones in the hands, especially the fingers, leading to permanent deformity and disability. In both psoriasis and psoriatic arthritis, disease flares may alternate with periods of remission.

Psoriatic arthritis occurs when the body's immune system begins to attack healthy cells and tissue. The abnormal immune response causes inflammation in the joints as well as overproduction of skin cells. It's not entirely clear why the immune system turns on healthy tissue, but it seems likely that both genetic and environmental factors play a role. Many people with psoriatic arthritis have a family history of either psoriasis or psoriatic arthritis. Researchers have discovered certain genetic markers that appear to be associated with psoriatic arthritis. Physical trauma or something in the environment, such as a viral or bacterial infection, may trigger psoriatic arthritis in people with an inherited tendency.

Ankylosing Spondylitis

In some embodiments, provided peptides are used in the treatment of ankylosing spondylitis. Ankylosing spondylitis is an inflammatory disease that can cause some of the vertebrae in the spine to fuse together. This fusing makes the spine less flexible and can result in a hunched-forward posture. A severe case of ankylosing spondylitis can make it impossible for someone to lift their head high enough to see forward. Ankylosing spondylitis affects men more often than women.

Early signs and symptoms of ankylosing spondylitis may include pain and stiffness in the lower back and hips, especially in the morning and after periods of inactivity. These symptoms may come on so gradually that one doesn't notice them at first. Over time, symptoms may worsen, improve or stop completely at irregular intervals. The areas of the body most commonly affected are: the joint between the base of the spine and the pelvis, the vertebrae in the lower back, the places where tendons and ligaments attach to bones, mainly in the spine, but sometimes along the back of the heel, the cartilage between the breastbone and ribs, hip and shoulder joints.

Ankylosing spondylitis has no known specific cause, though genetic factors seem to be involved. In particular, people who have a gene called HLA-B27 are at significantly increased risk of developing ankylosing spondylitis. As ankylosing spondylitis worsens and the inflammation persists, new bone forms as part of the body's attempt to heal. This new bone gradually bridges the gap between vertebrae and eventually fuses sections of vertebrae together. Those parts of the spine become stiff and inflexible. Fusion can also stiffen the rib cage, restricting lung capacity and function.

Vasculitis

In some embodiments, provided peptides are used in the treatment of vasculitis. Vasculitis is an inflammation of the blood vessels. Vasculitis causes changes in the walls of the blood vessels, including thickening, weakening, narrowing and scarring. There are many types of vasculitis. Some forms last only a short time (acute) while others are long lasting (chronic). Vasculitis, which is also known as angiitis and arteritis, can be so severe that the tissues and organs supplied by the affected vessels don't get enough blood. This shortage of blood can result in organ and tissue damage, even death. Vasculitis can affect anyone, though some types of vasculitis are more common among certain groups. Some forms of vasculitis improve on their own, but others require treatment—often including taking medications for an extended period of time.

The signs and symptoms of vasculitis vary depending on which blood vessels and, as a result, which organ systems are affected. However, general signs and symptoms that many people with vasculitis experience include: fever, fatigue, weight loss, muscle and joint pain, loss of appetite, and nerve problems, such as numbness or weakness. Signs and symptoms for some types of vasculitis include:

Behcet's syndrome: This condition causes inflammation of the arteries and veins, and often appears in people in their 20s and 30s. Signs and symptoms include mouth and genital ulcers, eye inflammation, and acne-like lesions on the skin.

Buerger's disease: Also called thromboangiitis obliterans, this condition causes inflammation and clots in the blood vessels in the extremities. Signs and symptoms can include pain in the hands, arms, feet and legs, and ulcers on the fingers and toes. This disorder is strongly associated with cigarette smoking.

Churg-Strauss syndrome: This condition, also known as allergic granulomatosis and allergic angiitis, most commonly affects the blood vessels in the lungs. It's often associated with asthma.

Cryoglobulinemia: This condition is often associated with hepatitis C infections. Signs and symptoms include a rash called purpura on the lower extremities, arthritis, weakness and nerve damage (neuropathy).

Giant cell arteritis: This condition, which usually occurs in people older than 50, is an inflammation of the arteries in the head, especially the temples. Giant cell arteritis can cause headaches, scalp tenderness, jaw pain while chewing, blurred or double vision, and even blindness. Giant cell arteritis is often associated with another type of inflammatory condition called polymyalgia rheumatica (PMR). PMR causes pain in and inflammation of the large joints, such as the shoulders and hips. Signs and symptoms include pain and stiffness in the muscles of the hips, thighs, shoulders, upper arms and neck.

Henoch-Schonlein purpura: This condition is caused by inflammation of the blood vessels of the skin, joints, bowel and kidneys. Signs and symptoms can include abdominal pain, blood in the urine, joint pain, and a rash called purpura on the buttocks, legs and feet. Henoch-Schonlein usually affects children, but it can occur at any age.

Hypersensitivity vasculitis: The primary sign of hypersensitivity vasculitis is red spots on the skin. It can be triggered by an allergy, most often to a medication or an infection.

Kawasaki disease: Also known as mucocutaneous lymph node syndrome, this condition most often affects children younger than 5 years of age. Signs and symptoms include fever, skin rash and eye inflammation.

Microscopic polyangiitis: This form of vasculitis affects small-sized blood vessels in the kidneys, lungs and skin. Signs and symptoms include skin lesions, fever, unintentional weight loss, glomerulonephritis—inflammation of the small blood vessels in the kidneys—and nerve damage.

Polyarteritis nodosa: This form of vasculitis affects medium-sized blood vessels in many different parts of the body, including the skin, heart, kidneys, peripheral nerves, muscles and intestines. Signs and symptoms include a rash called purpura, skin ulcers, muscle and joint pain, abdominal pain, and kidney problems.

Takayasu's arteritis: This form of vasculitis includes the largest arteries in the body, including the aorta, and typically occurs in young women. Signs and symptoms include a feeling of numbness or cold in the extremities, decreased or absent pulses, high blood pressure, headaches, and visual disturbances.

Granulomatosis with polyangiitis (Wegener's): Formerly known as Wegener's granulomatosis, granulomatosis with polyangiitis causes inflammation of the blood vessels in the nose, sinuses, throat, lungs and kidneys. Signs and symptoms can include nasal stuffiness, chronic sinus infections and nosebleeds. The kidneys are often affected, though most people won't have any noticeable symptoms until the damage is more advanced.

Vasculitis occurs when the immune system mistakenly sees blood vessel cells as foreign. The immune system then attacks those cells as if they were an invader, such as a bacteria or virus. It's not always clear why this happens, but an infection, some cancers, certain immune system disorders or an allergic reaction may serve as the trigger. Blood vessels affected by vasculitis become inflamed, which can cause the layers of the blood vessel wall to thicken. This narrows the blood vessels, reducing the amount of blood—and therefore oxygen and vital nutrients—that reaches the body's tissues. In some cases, a blood clot may form in an affected blood vessel, obstructing blood flow. Sometimes instead of becoming narrower, a blood vessel may weaken and form a bulge (aneurysm), a potentially life-threatening condition. For many of its forms, the cause of vasculitis is unknown. These forms of vasculitis are called primary vasculitis. Forms of vasculitis for which an underlying disease is the cause are called secondary vasculitis. Examples of causes of secondary vasculitis include: infections, immune system diseases, allergic reactions, and blood cell cancers.

Complications of vasculitis depend on the type of vasculitis a person has. In general, complications that can occur include: organ damage (some types of vasculitis can be severe, causing damage to major organs and recurring episodes of vasculitis (Even when treatment for vasculitis is initially successful, the condition may recur and require additional treatment; in other cases, vasculitis may never completely go away and requires ongoing treatment).

Multiple Sclerosis

In some embodiments, provided peptides are used in the treatment of multiple sclerosis (MS). Multiple sclerosis is a potentially debilitating disease in which the body's immune system eats away at the protective sheath (myelin) that covers the nerves. Damage to myelin causes interference in the communication between the brain, spinal cord and other areas of the body. This condition may result in deterioration of the nerves themselves, a process that's not reversible.

Symptoms of multiple sclerosis vary, depending on the location of affected nerve fibers. Multiple sclerosis symptoms may include: numbness or weakness in one or more limbs, partial or complete loss of central vision, usually in one eye, often with pain during eye movement (optic neuritis), double vision or blurring of vision, tingling or pain in parts of the body, electric-shock sensations that occur with certain head movements, tremor, lack of coordination or unsteady gait, slurred speech, fatigue, and dizziness. Heat sensitivity is common in people with multiple sclerosis. Small increases in body temperature can trigger or worsen multiple sclerosis symptoms. Most people with multiple sclerosis, particularly in the beginning stages of the disease, experience relapses of symptoms, which are followed by periods of complete or partial remission of symptoms. Some people have a benign form of multiple sclerosis. In this form of the disease, the condition remains stable and often doesn't progress to serious forms of MS after the initial attack. In some cases, people with multiple sclerosis may also develop: muscle stiffness of spasms, paralysis, most typically in the legs, problems with bladder, bowel or sexual function, mental changes, such as forgetfulness or difficulties concentrating, depression and epilepsy.

The cause of multiple sclerosis is unknown. It's believed to be an autoimmune disease, in which the body's immune system attacks its own tissues. In multiple sclerosis, this process destroys myelin—the fatty substance that coats and protects nerve fibers in the brain and spinal cord. Myelin can be compared to the insulation on electrical wires. When myelin is damaged, the messages that travel along that nerve may be slowed or blocked. Doctors and researchers don't understand why multiple sclerosis develops in some people and not others. A combination of factors, ranging from genetics to childhood infections, may play a role.

Inflammatory Bowel Disease (IBD)

In some embodiments, provided peptides are used in the treatment of inflammatory bowel disease (IBD). Inflammatory bowel disease (IBD) involves chronic inflammation of all or part of the digestive tract. IBD primarily includes ulcerative colitis and Crohn's disease. IBD can be painful and debilitating, and sometimes leads to life-threatening complications. Ulcerative colitis is an inflammatory bowel disease that causes long-lasting inflammation in part of the digestive tract. Symptoms usually develop over time, rather than suddenly. Ulcerative colitis usually affects only the innermost lining of the large intestine (colon) and rectum. It occurs only through continuous stretches of the colon. Crohn's disease is an inflammatory bowel disease that causes inflammation anywhere along the lining of the digestive tract, and often spreads deep into affected tissues. This can lead to abdominal pain, severe diarrhea and even malnutrition. The inflammation caused by Crohn's disease can involve different areas of the digestive tract in different people. Collagenous colitis and lymphocytic colitis also are considered inflammatory bowel diseases, but are usually regarded separately from classic inflammatory bowel disease.

Inflammatory bowel disease symptoms vary, depending on the severity of inflammation and where it occurs. Ulcerative colitis is classified according to its signs and symptoms. In ulcerative proctitis, inflammation is confined to the area closest to the anus (rectum), and for some people, rectal bleeding may be the only sign of the disease. Others may have rectal pain, a feeling of urgency or have frequent, small bowel movements. This form of ulcerative colitis tends to be the mildest. In proctosigmoiditis, the rectum and the lower end of the colon, known as the sigmoid colon are involved. Bloody diarrhea, abdominal cramps and pain, and an inability to move the bowels in spite of the urge to do so (tenesmus) are common problems associated with this form of the disease. In left-sided colitis, inflammation extends from the rectum up through the sigmoid and descending colon, which are located in the upper left part of the abdomen. Signs and symptoms include bloody diarrhea, abdominal cramping and pain on the left side, and unintended weight loss. In pancolitis, more than the left colon, and often the entire colon, are affected. Pancolitis causes bouts of bloody diarrhea that may be severe, abdominal cramps and pain, fatigue, and significant weight loss. Fulminant colitis is a rare, life-threatening form of colitis that affects the entire colon and causes severe pain, profuse diarrhea and, sometimes, dehydration and shock. People with fulminant colitis are at risk of serious complications, including colon rupture and toxic megacolon, a condition that causes the colon to rapidly expand. The course of ulcerative colitis varies, with periods of acute illness often alternating with periods of remission. Most people with a milder condition, such as ulcerative proctitis, won't go on to develop more severe signs and symptoms. IBD may lead to one or more of the following complications: bowel obstruction, ulcers, fistulas, anal fissure, malnutrition, colon cancer, and other health problems such as arthritis, inflammation of eyes or skin, clubbing of fingernails, kidney stones, gallstones, inflammation of the bile ducts, and osteoporosis.

Crohn's Disease

In some embodiments, provided peptides are used in the treatment of Crohn's disease. Crohn's disease is an inflammatory bowel disease (IBD). It causes inflammation of the lining of the digestive tract, which can lead to abdominal pain, severe diarrhea and even malnutrition. Inflammation caused by Crohn's disease can involve different areas of the digestive tract in different people. The inflammation caused by Crohn's disease often spreads deep into the layers of affected bowel tissue. Like ulcerative colitis, another common IBD, Crohn's disease can be both painful and debilitating, and sometimes may lead to life-threatening complications.

Inflammation of Crohn's disease may involve different areas in different people. In some people, just the small intestine is affected. In others, it's confined to the colon (part of the large intestine). The most common areas affected by Crohn's disease are the last part of the small intestine (ileum) and the colon. Inflammation may be confined to the bowel wall, which can lead to scarring (stenosis), or inflammation may spread through the bowel wall (fistula). Signs and symptoms of Crohn's disease can range from mild to severe and may develop gradually or come on suddenly, without warning. A person may also have periods of time when they have no signs or symptoms (remission). When the disease is active, signs and symptoms may include: diarrhea, abdominal pain and cramping (may include nausea and vomiting), bloody stool, ulcers, and reduced appetite and weight loss. Others signs and symptoms include: fever, arthritis, eye inflammation, mouth sores, skin disorders, inflammation of the liver or bile ducts, and, in children, delayed growth or sexual development. Additionally, Crohn's disease may lead to one or more of the following complications: bowel obstruction, ulcers, fistulas, anal fissure, malnutrition, color cancer, and other health problems such as arthritis, inflammation of eyes or skin, clubbing of fingernails, kidney stones, gallstones, inflammation of the bile ducts, and osteoporosis.

Organ System Specific Inflammation

In some embodiments, provided peptides are used in the treatment of inflammation associated with inflammatory conditions of the skin (e.g., psoriasis), cardiovascular system (e.g., atherosclerosis), nervous system (e.g., Alzheimer's disease), liver (e.g., hepatitis), kidney (e.g., nephritis) and pancreas (e.g., pancreatitis).

Nervous System

In some embodiments, provided peptides are used in the treatment of inflammation associated with inflammatory conditions of the nervous system (e.g. Alzheimer's disease). Alzheimer's disease is a progressive disease that destroys memory and other important mental functions. Ifs the most common cause of dementia—a group of brain disorders that results in the loss of intellectual and social skills. These changes are severe enough to interfere with day-to-day life. In Alzheimer's disease, the connections between brain cells and the brain cells themselves degenerate and die, causing a steady decline in memory and mental function.

At first, increasing forgetfulness or mild confusion may be the only symptoms of Alzheimer's disease that are noticed. But over time, the disease robs a person of more of their memory, especially recent memories. The rate at which symptoms worsen varies from person to person. In a person with Alzheimer's, unusual difficulty remembering things and organizing thoughts may be the first things they notice. On the other hand, some people with Alzheimer's may not recognize that anything is wrong, even when changes are noticeable to family members, close friends or co-workers. Brain changes associated with Alzheimer's disease lead to growing trouble with memory, disorientation and misinterpreting spatial relationships, speaking and writing, thinking and reasoning, making judgments and decisions, planning and performing familiar tasks and changes in personality and behavior. Memory loss, impaired judgment and other cognitive changes caused by Alzheimer's can complicate treatment for other health conditions. A person with Alzheimer's disease may not be able to: communicate that he or she is experiencing pain—for example, from a dental problem, report symptoms of another illness, follow a prescribed treatment plan, or notice or describe medication side effects. As Alzheimer's disease progresses to later stages, brain changes begin to affect physical functions, such as swallowing, balance, and bowel and bladder control. These effects can increase vulnerability to additional health problems such as: pneumonia and other infections and injuries from falls.

Scientists believe that for most people, Alzheimer's disease results from a combination of genetic, lifestyle and environmental factors that affect the brain over time. Less than 5 percent of the time, Alzheimer's is caused by specific genetic changes that virtually guarantee a person will develop the disease. Although the causes of Alzheimer's are not yet fully understood, its effect on the brain is clear. Alzheimer's disease damages and kills brain cells. A brain affected by Alzheimer's disease has many fewer cells and many fewer connections among surviving cells than does a healthy brain. As more and more brain cells die, Alzheimer's leads to significant brain shrinkage. When doctors examine Alzheimer's brain tissue under the microscope, they see two types of abnormalities that are considered hallmarks of the disease: plaques (clumps of a protein called beta-amyloid that may damage and destroy brain cells in several ways, including interfering with cell-to-cell communication) and tangles (abnormal twists of tau proteins that lead to a failure in the internal support and nutrient transport system upon which brain cells depend).

Liver

In some embodiments, provided peptides are used in the treatment of inflammation associated with inflammatory conditions of the liver (e.g. hepatitis). Hepatitis is a medical condition defined by the inflammation of the liver and characterized by the presence of inflammatory cells in the tissue of the organ. Hepatitis may occur with limited or no symptoms, but often leads to jaundice, anorexia (poor appetite) and malaise. Hepatitis is acute when it lasts less than six months and chronic when it persists longer. A group of viruses known as the hepatitis viruses cause most cases of hepatitis worldwide, but hepatitis can also be caused by toxic substances (notably alcohol, certain medications, some industrial organic solvents and plants), other infections and autoimmune diseases.

Initial features are of nonspecific flu-like symptoms, common to almost all acute viral infections and may include malaise, muscle and joint aches, fever, nausea or vomiting, diarrhea, and headache. More specific symptoms, which can be present in acute hepatitis from any cause, are: profound loss of appetite, aversion to smoking among smokers, dark urine, yellowing of the eyes and skin (i.e., jaundice) and abdominal discomfort. Physical findings are usually minimal, apart from jaundice in a third and tender hepatomegaly (swelling of the liver) in about 10%. Some exhibit lymphadenopathy (enlarged lymph nodes) or splenomegaly (enlargement of the spleen). Acute viral hepatitis is more likely to be asymptomatic in younger people. Symptomatic individuals may present after convalescent stage of 7 to 10 days, with the total illness lasting 2 to 6 weeks. A small proportion of people with acute hepatitis progress to acute liver failure, in which the liver is unable to clear harmful substances from the circulation (leading to confusion and coma due to hepatic encephalopathy) and produce blood proteins (leading to peripheral edema and bleeding). This may become life-threatening and occasionally requires a liver transplant.

Chronic hepatitis often leads to nonspecific symptoms such as malaise, tiredness and weakness, and often leads to no symptoms at all. It is commonly identified on blood tests performed either for screening or to evaluate nonspecific symptoms. The occurrence of jaundice indicates advanced liver damage. On physical examination there may be enlargement of the liver. Extensive damage to and scarring of liver (i.e. cirrhosis) leads to weight loss, easy bruising and bleeding tendencies, peripheral edema (swelling of the legs) and accumulation of ascites (fluid in the peritoneal cavity). Eventually, cirrhosis may lead to various complications: esophageal varices (enlarged veins in the wall of the esophagus that can cause life-threatening bleeding) hepatic encephalopathy (confusion and coma) and hepatorenal syndrome (kidney dysfunction). Acne, abnormal menstruation, lung scarring, inflammation of the thyroid gland and kidneys may be present in women with autoimmune hepatitis.

Kidney

In some embodiments, provided peptides are used in the treatment of inflammation associated with inflammatory conditions of the kidney (e.g. nephritis). Nephritis is inflammation of the nephrons in the kidneys. Glomerulonephritis is inflammation of the glomeruli. (When the term "nephritis" is used without qualification, this is often the condition meant.) Glomeruli remove excess fluid, electrolytes and waste from the bloodstream and pass them into the urine. Also called glomerular disease, glomerulonephritis can be acute—a sudden attack of inflammation—or chronic—coming on gradually. Interstitial nephritis or tubulo-interstitial nephritis is inflammation of the spaces between renal tubules.

If glomerulonephritis occurs on its own, it's known as primary glomerulonephritis. If another disease, such as lupus or diabetes, is the cause, it's called secondary glomerulonephritis. If severe or prolonged, the inflammation associated with glomerulonephritis can damage the kidneys. Signs and symptoms of glomerulonephritis may depend on the cause and whether one has the acute or chronic form. The first indication that something is wrong may come from symptoms or from the results of a routine urinalysis. Signs and symptoms may include: pink or cola-colored urine from red blood cells in the urine (hematuria), foamy urine due to excess protein (proteinuria), high blood pressure (hypertension), fluid retention (edema) with swelling evident in the face, hands, feet and abdomen, and fatigue from anemia or kidney failure. Glomerulonephritis can damage the kidneys so that they lose their filtering ability. This can lead to the accumulation of dangerous levels of fluid, electrolytes and waste in the body (called kidney failure) and deprive the bloodstream of necessary protein. Complications of glomerulonephritis may include: acute kidney failure, chronic kidney failure, high blood pressure and nephrotic syndrome.

Pancreas

In some embodiments, provided peptides are used in the treatment of inflammation associated with inflammatory conditions of the pancreas (e.g. pancreatitis). Pancreatitis is inflammation in the pancreas. The pancreas is a long, flat gland that sits tucked behind the stomach in the upper abdomen. The pancreas produces enzymes that help digestion and hormones that help regulate the way the body processes sugar (glucose). Pancreatitis can occur as acute pancreatitis—meaning it appears suddenly and lasts for days. Or pancreatitis can occur as chronic pancreatitis, which describes pancreatitis that occurs over many years. Mild cases of pancreatitis may go away without treatment, but severe cases can cause life-threatening complications.

Signs and symptoms of pancreatitis may vary, depending on which type is experienced. Acute pancreatitis signs and symptoms include: upper abdominal pain, abdominal pain that radiates to the back, abdominal pain that feels worse after eating, nausea, vomiting, and tenderness when touching the abdomen. Chronic pancreatitis signs and symptoms include: upper abdominal pain, indigestion, losing weight without trying and oily, smelly stools (steatorrhea). Pancreatitis can cause serious complications, including: breathing problems, diabetes, infection, kidney failure, malnutrition, pancreatic cancer, and pseudocyst.

Pancreatitis occurs when digestive enzymes produced in the pancreas become activated while inside the pancreas, causing damage to the organ. During normal digestion, the inactivated pancreatic enzymes move through ducts in the pancreas and travel to the small intestine, where the enzymes become activated and help with digestion. In pancreatitis, the enzymes become activated while still in the pancreas. This causes the enzymes to irritate the cells of the pancreas, causing inflammation and the signs and symptoms associated with pancreatitis. With repeated bouts of acute pancreatitis, damage to the pancreas can occur and lead to chronic pancreatitis. Scar tissue may form in the pancreas, causing loss of function. A poorly functioning pancreas can cause digestion problems and diabetes. A number of causes have been identified for acute pancreatitis and chronic pancreatitis, including: alcoholism, gallstones, abdominal surgery, certain medications, cigarette smoking, cystic fibrosis, endoscopic retrograde cholangiopancreatography (ERCP) (when used to treat gallstones), family history of pancreatitis, high calcium levels in the blood (hypercalcemia), high levels of parathyroid hormone in the blood (hyperparathyroidism), high triglyceride levels in the blood (hypertriglyceridemia), infection, injury to the abdomen, and pancreatic cancer.

Cardiovascular Disorders

In some embodiments, provided peptides are used in the treatment of inflammation associated with cardiovascular disorders (e.g., cholesterol metabolic disorders, oxygen free radical injury, ischemia, pulmonary fibrosis, idiopathic pulmonary fibrosis, reperfusion injury, acute vaso-occlusive crisis in sickle cell anemia).

Pulmonary Fibrosis

In some embodiments, provided peptides are used in the treatment of pulmonary fibrosis. Pulmonary fibrosis occurs when lung tissue becomes damaged and scarred. This thickened, stiff tissue makes it more difficult for the lungs to work properly. As pulmonary fibrosis worsens, a person become progressively more short of breath.

Signs and symptoms of pulmonary fibrosis include: shortness of breath (dyspnea), a dry cough, fatigue, unexplained weight loss, and aching muscles and joints. The course of pulmonary fibrosis—and the severity of symptoms—can vary considerably from person to person. Some people become ill very quickly with severe disease. Others have more moderate symptoms that worsen over months or years. Complications of pulmonary fibrosis may include: high blood pressure in the lungs (pulmonary hypertension), right-sided heart failure (cor pulmonale), respiratory failure and lung cancer.

Pulmonary fibrosis scars and thickens the tissue around and between the air sacs (alveoli) in the lungs. This makes it more difficult for oxygen to pass into the bloodstream. The damage can be caused by many different things—including airborne toxins in the workplace, certain lung diseases and even some types of medical treatments. Long-term exposure to a number of toxins and pollutants can damage the lungs. These may include: silica dust, asbestos fibers, grain dust, and bird and animal droppings. Some people who receive radiation therapy for lung or breast cancer show signs of lung damage months or sometimes years after the initial treatment. The severity of the damage depends on: how much of the lung was exposed to radiation, the total amount of radiation administered, whether chemotherapy also was used, and the presence of underlying lung disease. Many drugs can damage the lungs, especially: chemotherapy drugs, heart medications, and some antibiotics. Lung damage can also result from: tuberculosis, pneumonia, systemic lupus erythematosus, rheumatoid arthritis, sarcoidosis, and scleroderma. The list of substances and conditions that can lead to pulmonary fibrosis is long. Even so, in most cases, the cause is never found. Pulmonary fibrosis with no known cause is called idiopathic pulmonary fibrosis. Researchers have several theories about what might trigger idiopathic pulmonary fibrosis, including viruses and exposure to tobacco smoke. Additionally, because one type of idiopathic pulmonary fibrosis runs in families, heredity also is thought to play a role.

Reperfusion Injury

In some embodiments, provided peptides are used in the treatment of reperfusion injury. Reperfusion injury is the tissue damage caused when blood supply returns to the tissue after a period of ischemia or lack of oxygen. The absence of oxygen and nutrients from blood during the ischemic period creates a condition in which the restoration of circulation results in inflammation and oxidative damage through the induction of oxidative stress rather than restoration of normal function.

The inflammatory response is partially responsible for the damage of reperfusion injury. White blood cells, carried to the area by the newly returning blood, release a host of inflammatory factors such as interleukins as well as free radicals in response to tissue damage.[1] The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. White blood cells may also bind to the endothelium of small capillaries, obstructing them and leading to more ischemia.

Reperfusion injury plays a part in the brain's ischemic cascade, which is involved in stroke and brain trauma. Similar failure processes are involved in brain failure following reversal of cardiac arrest; control of these processes is the subject of ongoing research. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound. In prolonged ischemia (60 minutes or more), hypoxanthine is formed as breakdown product of ATP metabolism. The enzyme xanthine dehydrogenase acts in reverse, that is as a xanthine oxidase as a result of the higher availability of oxygen. This oxidation results in molecular oxygen being converted into highly reactive superoxide and hydroxyl radicals. Xanthine oxidase also produces uric acid, which may act as both a pro-oxidant and as a scavenger of reactive species such as peroxynitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling. Reperfusion injury is a primary concern in liver transplantation surgery.

Acute Vaso-Occlusive Crisis in Sickle Cell Anemia

In some embodiments, provided peptides are used in the treatment of pacute vaso-occlusive crisis. Sickle cell anemia is an inherited form of anemia—a condition in which there aren't enough healthy red blood cells to carry adequate oxygen throughout the body. Normally, red blood cells are flexible and round, moving easily through blood vessels. In sickle cell anemia, the red blood cells become rigid and sticky and are shaped like sickles or crescent moons. These irregularly shaped cells can get stuck in small blood vessels, which can slow or block blood flow and oxygen to parts of the body. This decreased or blocked circulation is called vaso-occlusive crisis.

The most common complaint is of pain, and recurrent episodes may cause irreversible organ damage. One of the most severe forms is the acute chest syndrome, which occurs as a result of infarction of the lung parenchyma; this infarction can rapidly result in death of the patient if not properly managed immediately.

The management of an acute event of vaso-occlusive crisis is the use of potent analgesic (opioids), rehydration with normal saline or ringers lactate, treatment of malaria (whether symptomatic or not) using Atemisinin Combination Therapy, and use of adjunct therapy such as oxygen via face mask.

Chronic Obstructive Pulmonary Disease (COPD)

In some embodiments, provided peptides are used in the treatment of Chronic obstructive pulmonary disease (COPD). COPD refers to a group of lung diseases that block airflow and make breathing difficult. Emphysema and chronic bronchitis are the two most common conditions that make up COPD. Chronic bronchitis is an inflammation of the lining of the bronchial tubes, which carry air to and from the lungs. Emphysema occurs when the air sacs (alveoli) at the end of the smallest air passages (bronchioles) in the lungs are gradually destroyed.

Symptoms of COPD often don't appear until significant lung damage has occurred, and they usually worsen over time. For chronic bronchitis, the main symptom is a cough that a person has at least three months a year for two consecutive years. Other signs and symptoms of COPD include: shortness of breath, especially during physical activities, wheezing, chest tightness, having to clear one's throat first thing in the morning, due to excess mucus in the lungs, a chronic cough that produces sputum that may be clear, white, yellow or greenish, blueness of the lips or fingernail beds (cyanosis), frequent respiratory infections, lack of energy, and unintended weight loss (in later stages). People with COPD are also likely to experience episodes called exacerbations, during which their symptoms become worse and persist for days or longer. Complications of COPD include: respiratory infections, high blood pressure, heart problems, lung cancer and depression.

The main cause of COPD is tobacco smoking. However, there are likely other factors at play in the development of COPD, such as a genetic susceptibility to the disease, because only about 20 percent of smokers develop COPD. Other irritants can cause COPD, including cigar smoke, secondhand smoke, pipe smoke, air pollution and workplace exposure to dust, smoke or fumes. In the developing world, COPD often occurs in women exposed to fumes from burning fuel for cooking and heating in poorly ventilated homes. In about 1 percent of people with COPD, the disease results from a genetic disorder that causes low levels of a protein called alpha-1-antitrypsin. Alpha-1-antitrypsin (AAt) is made in the liver and secreted into the bloodstream to help protect the lungs. Alpha-1-antitrypsin deficiency can affect the liver as well as the lungs. Damage to the liver can occur in infants and children, not just adults with long smoking histories. For adults with COPD related to AAt deficiency, treatment options are the same as those for people with more common types of COPD. Some people can be treated by replacing the missing AAt protein, which may prevent further damage to the lungs.

For patients whose COPD is linked to smoking, the most essential step in any treatment plan for COPD is to stop all smoking. There several kinds of medications to treat the symptoms and complications of COPD and they include: bronchodilators, inhaled steroids, combination inhalers, oral steroids, phosphodiesterase-4 inhibitors, theophylline and antibiotics. Additional therapies for people with moderate or severe COPD include: oxygen therapy and a pulmonary rehabilitation program. Surgery is an option for some people with some forms of severe emphysema who aren't helped sufficiently by medications alone. In lung volume reduction surgery, the surgeon removes small wedges of damaged lung tissue. This creates extra space in the chest cavity so that the remaining lung tissue and the diaphragm work more efficiently. Lung transplantation may be an option for certain people who meet specific criteria.

Cystic Fibrosis

In some embodiments, provided peptides are used in the treatment of cystic fibrosis. Cystic fibrosis is a life-threatening disorder that causes severe damage to the lungs and digestive system. An inherited condition, cystic fibrosis affects the cells that produce mucus, sweat and digestive juices. These secreted fluids are normally thin and slippery. But in cystic fibrosis, a defective gene causes the secretions to become thick and sticky. Instead of acting as a lubricant, the secretions plug up tubes, ducts and passageways, especially in the lungs and pancreas. Cystic fibrosis signs and symptoms vary, depending on the severity of the disease. Even in the same person, symptoms may worsen or improve as time passes. In some children, symptoms begin during infancy. Other people may not experience symptoms until adolescence or adulthood. Screening of newborns for cystic fibrosis is now performed in all 50 states. As a result, the condition is diagnosed within the first month of life, before symptoms develop. For people born before newborn screening was performed, it's important to be aware of the signs and symptoms of cystic fibrosis.

People with cystic fibrosis tend to have a higher than normal level of salt in their sweat. Parents often can taste the salt when they kiss their children. Most of the other signs and symptoms of cystic fibrosis affect the respiratory system or the digestive system. Thick and sticky mucus clogging the passageways that carry air in and out of the lungs lead to respiratory signs and symptoms including: a persistent cough that produces thick spit (sputum) and mucus, wheezing, breathlessness, a decreased ability to exercise, repeated lung infections, and inflamed nasal passages or a stuffy nose. The thick mucus can also block tubes that carry digestive enzymes from the pancreas to the small intestine. Without those enzymes, the intestines can't fully absorb the nutrients from food, resulting in digestive signs and symptoms that include: foul-smelling, greasy stools, poor weight gain and growth, intestinal blockage, particularly in newborns (meconium ileus), and severe constipation. The sticky mucus associated with cystic fibrosis causes many complications, the most common in the respiratory, digestive and reproductive systems. Respiratory system complications can include: bronchiectasis, chronic infections, nasal polyps, coughing up blood, pneumothorax, collapsed lung and respiratory failure. Digestive system complications can include: nutritional deficiencies, diabetes, blocked bile duct, rectal prolapse and intussusception. Almost all men with cystic fibrosis are infertile because the tube that connects the testes and prostate gland (vas deferens) is either blocked with mucus or missing entirely. Certain fertility treatments and surgical procedures sometimes make it possible for men with cystic fibrosis to become fathers. Although women with cystic fibrosis may be less fertile than other women, it's possible for them to conceive and to have successful pregnancies. Other complications of cystic fibrosis include osteoporosis and electrolyte imbalances.

Acute Inflammatory Conditions

In some embodiments, provided peptides are used in the treatment of inflammation associated with acute inflammatory conditions (e.g., endotoxemia, sepsis and septicaemia, toxic shock syndrome and infectious disease (e.g., myocarditis, cardiomyopathy, acute endocarditis, pericarditis);

Acute Endocarditis

In some embodiments, provided peptides are used in the treatment of acute endocarditis. Endocarditis is an infection of the inner lining of the heart (endocardium). Endocarditis typically occurs when bacteria or other germs from another part of the body, such as the mouth, spread through the bloodstream and attach to damaged areas in the heart. Left untreated, endocarditis can damage or destroy heart valves and can lead to life-threatening complications. Endocarditis is uncommon in people with healthy hearts. People at greatest risk of endocarditis have a damaged heart valve, an artificial heart valve or other heart defects.

Endocarditis may develop slowly or suddenly—depending on what's causing the infection and whether the person has any underlying heart problems. The infection can infect different people differently, so signs and symptoms vary. They may include: fever, chills, a new or changed heart murmur, fatigue, aching joints and muscles, night sweats, shortness of breath, paleness, persistent cough, swelling of the feet, legs or abdomen, unexplained weight loss, blood in the urine, tenderness in the spleen, Osler's nodes and petechiae. Endocarditis can cause several major complications, including: stroke and organ damage, infections in other parts of the body and heart failure.

Endocarditis occurs when germs enter the bloodstream, travel to the heart, and attach to abnormal heart valves or damaged heart tissue. Bacteria cause most cases, but fungi or other microorganisms also may be responsible. Sometimes the culprit is one of many common bacteria that live in the mouth, throat or other parts of the body. The offending organism may enter the bloodstream through: everyday oral activities, an infection of other medical condition, catheters or needles, or certain dental procedures. Typically, the immune system destroys bacteria that make it into the bloodstream. Even if bacteria reach the heart, they may pass through without causing an infection. Most people who develop endocarditis have a diseased or damaged heart valve—an ideal spot for bacteria to settle. This damaged tissue in the endocardium provides bacteria with the roughened surface they need to attach and multiply.

Pericarditis

In some embodiments, provided peptides are used in the treatment of pericarditis. Pericarditis is a swelling and irritation of the pericardium, the thin sac-like membrane that surrounds the heart. Pericarditis often causes chest pain and sometimes other symptoms. Pericarditis is usually sudden and short-lived (acute).

Acute pericarditis usually lasts less than a few weeks. Chronic pericarditis usually lasts six months or longer. In acute pericarditis, the most common symptom is sharp, stabbing chest pain behind the breastbone or in the left side of the chest. However, some people with acute pericarditis describe their chest pain as dull, achy or pressure-like instead, and of varying intensity. The pain of acute pericarditis may travel into the left shoulder and neck. It often intensifies when one lies down or inhales deeply. Coughing, taking a deep breath or swallowing food also may make the pain worse. Sitting up and leaning forward can often ease the pain. At times, it may be difficult to distinguish pericardial pain from the pain that occurs with a heart attack. Chronic pericarditis is usually associated with chronic inflammation and may result in fluid around the heart (pericardial effusion). The most common symptom of chronic pericarditis is chest pain. Depending on the type, signs and symptoms of pericarditis may include some or all of the following:

sharp, piercing chest pain over the center or left side of the chest, shortness of breath when reclining, low-grade fever, an overall sense of weakness, fatigue or feeling sick, dry cough, and abdominal or leg swelling. Many of the symptoms of pericarditis are similar to those of other heart and lung conditions. For example, although the cause of acute chest pain may be pericarditis, the original cause could be a heart attack or a blood clot of the lungs (pulmonary embolus). Complications of pericarditis can include constrictive pericarditis (permanent thickening, scarring and contraction of the pericardium) and cardiac tamponade (dramatic drop in blood pressure caused by excess fluid around the heart preventing the heart from filling and leaving the heart).

Adult Respiratory Distress Syndrome (ARDS)

In some embodiments, provided peptides are used in the treatment of acute respiratory distress syndrome (ARDS). Acute respiratory distress syndrome occurs when fluid builds up in the tiny, elastic air sacs (alveoli) in the lungs. More fluid in the lungs means less oxygen can reach the bloodstream. This deprives organs of the oxygen they need to function. Many people who develop ARDS don't survive. The risk of death increases with age and severity of illness. Of the people who do survive ARDS, some recover completely while others experience lasting damage to their lungs.

The signs and symptoms of ARDS can vary in intensity, depending on its cause and severity. They include: severe shortness of breath, labored and unusually rapid breathing, low blood pressure, and confusion and extreme tiredness. ARDS typically occurs in people who are already critically ill or who have significant injuries. ARDS is extremely serious, but thanks to improved treatments, more people are surviving it. However, many survivors end up with potentially serious—and sometimes lasting—complications, including: pulmonary fibrosis, collapsed lung (pneumothorax), blood clots, infections, abnormal lung function, and memory, cognitive and emotional problems.

The mechanical cause of ARDS is fluid leaked from the smallest blood vessels in the lungs into the tiny air sacs where blood is oxygenated. Normally, a protective membrane keeps this fluid in the vessels. Severe illness or injury, however, can cause inflammation that undermines the membrane's integrity, leading to the fluid leakage of ARDS. The most common underlying causes of ARDS include: sepsis, inhalation of harmful substances, severe pneumonia and head or chest injury.

Scleroderma

In some embodiments, provided peptides are used in the treatment of scleroderma. Scleroderma is a group of rare diseases that involve the hardening and tightening of the skin and connective tissue, the fibers that provide the framework and support for the body. In some people, scleroderma affects only the skin. But in many people, scleroderma also harms structures beyond the skin, such as blood vessels, internal organs and the digestive tract. Signs and symptoms vary, depending on which structures are affected. Scleroderma affects women more often than men and most commonly occurs between the ages of 30 and 50. While there is no cure for scleroderma, a variety of treatments can ease symptoms and improve quality of life.

Scleroderma's signs and symptoms vary, depending on which parts of the body are involved. Nearly everyone who has scleroderma experiences a hardening and tightening of patches of skin. These patches may be shaped like ovals or straight lines. The number, location and size of the patches vary by type of scleroderma. Skin can appear shiny because it's so tight, and movement of the affected area may be restricted. One of the earliest signs of scleroderma is an exaggerated response to cold temperatures or emotional distress, which can cause numbness, pain or color changes in the fingers or toes. Called Raynaud's phenomenon, this condition also occurs in people who don't have scleroderma. In addition to acid reflux, which can damage the section of esophagus nearest the stomach, some people with scleroderma may also have problems absorbing nutrients if their intestinal muscles aren't moving food properly through the intestines. Rarely, scleroderma can affect the function of the heart, lungs or kidneys. These problems can become life-threatening.

Scleroderma complications range from mild to severe and can affect the: fingertips (the variety of Raynaud's phenomenon that occurs with scleroderma can be so severe that the restricted blood flow permanently damages the tissue at the fingertips, causing pits or skin sores (ulcers); in some cases, gangrene and amputation may follow), lungs (scarring of lung tissue (pulmonary fibrosis) can result in reduced lung function, reduced ability to breathe and reduced tolerance for exercise; patients can also develop high blood pressure in the arteries to the lungs (pulmonary hypertension)), kidneys (possibility of developing elevated blood pressure and an increased level of protein in the urine; more-serious effects of kidney complications may include renal crisis, which involves a sudden increase in blood pressure and rapid kidney failure), heart (scarring of heart tissue increases the risk of abnormal heartbeats (arrhythmias) and congestive heart failure, and can cause inflammation of the membranous sac surrounding the heart (pericarditis); scleroderma also can raise the pressure on the right side of the heart and cause it to wear out), teeth (severe tightening of facial skin can cause the mouth to become smaller and narrower, which may make it hard to brush the teeth or to even have them professionally cleaned; people who have scleroderma often don't produce normal amounts of saliva, so the risk of dental decay increases even more), digestive system (digestive problems associated with scleroderma can lead to acid reflux and difficulty swallowing—some describe feeling as if food gets stuck midway down the esophagus—as well as bouts of constipation alternating with episodes of diarrhea) and sexual function (men who have scleroderma often experience erectile dysfunction; scleroderma may also affect the sexual function of women, by decreasing sexual lubrication and constricting the vaginal opening).

Scleroderma results from an overproduction and accumulation of collagen in body tissues. Collagen is a fibrous type of protein that makes up the body's connective tissues, including the skin. Although doctors aren't sure what prompts this abnormal collagen production, the body's immune system appears to play a role. For unknown reasons, the immune system turns against the body, producing inflammation and the overproduction of collagen.

Systemic Lupus Erythematosis

In some embodiments, provided peptides are used in the treatment of systemic lupus erythmatosis. Lupus is a chronic inflammatory disease that occurs when the body's immune system attacks its own tissues and organs. Inflammation caused by lupus can affect many different body systems—including joints, skin, kidneys, blood cells, brain, heart and lungs. Lupus can be difficult to diagnose because its signs and symptoms often mimic those of other ailments. The most distinctive sign of lupus—a facial rash that resembles the wings of a butterfly unfolding across both cheeks—occurs in many but not all cases of lupus.

Lupus occurs when the immune system attacks healthy tissue in the body. It's likely that lupus results from a combination of genetics and environment. It appears that people with an inherited predisposition for lupus may develop the disease when they come into contact with something in the environment that can trigger lupus. The cause for lupus in most cases, however, is unknown. Some potential triggers include: sunlight (exposure to the sun may bring on lupus skin lesions or trigger an internal response in susceptible people) and medications (lupus can be triggered by certain types of anti-seizure medications, blood pressure medications and antibiotics; people who have drug-induced lupus usually see their symptoms go away when they stop taking the medication).

Inflammation caused by lupus can affect many areas of the body. Lupus can cause serious kidney damage, and kidney failure is one of the leading causes of death among people with lupus. Signs and symptoms of kidney problems may include generalized itching, chest pain, nausea, vomiting and leg swelling (edema). If the brain is affected by lupus, a person may experience headaches, dizziness, behavior changes, hallucinations, and even strokes or seizures. Many people with lupus experience memory problems and may have difficulty expressing their thoughts. Lupus can lead to blood problems, including anemia and increased risk of bleeding or blood clotting. It can also cause inflammation of the blood vessels (vasculitis). Having lupus increases a person's chances of developing an inflammation of the chest cavity lining (pleurisy), which can make breathing painful. Lupus can cause inflammation of the heart muscle, arteries or heart membrane (pericarditis). The risk of cardiovascular disease and heart attacks increases greatly as well. Lupus can also increase a person's risk of infection, cancer, bone tissue death (avascular necrosis) and pregnancy complications).

Sjogren's Syndrome

In some embodiments, provided peptides are used in the treatment of Sjogren's syndrome. Sjogren's syndrome is a disorder of the immune system identified by its two most common symptoms—dry eyes and a dry mouth. Sjogren's syndrome often accompanies other immune-system disorders, such as rheumatoid arthritis and lupus. In Sjogren's syndrome, the mucous membranes and moisture-secreting glands of the eyes and mouth are usually affected first—resulting in decreased production of tears and saliva. Although a person can develop Sjogren's syndrome at any age, most people are older than 40 at the time of diagnosis. The condition is much more common in women.

The two main symptoms of Sjogren's syndrome are dry eyes and dry mouth. The eyes may burn, itch or feel gritty, as if there's sand in them and the mouth may feel like it's full of cotton, making it difficult to swallow or speak. Some people with Sjogren's syndrome also experience one of more of the following: joint pain, swelling and stiffness, swollen salivary glands—particularly the set located behind the jaw and in front of the ears, skin rashes or dry skin, vaginal dryness, persistent dry cough and prolonged fatigue.

Sjogren's syndrome is an autoimmune disorder. This means that the immune system mistakenly attacks the body's own cells and tissues. Scientists aren't certain why some people develop Sjogren's syndrome and others don't. Certain genes put people at higher risk for the disorder, but it appears that a triggering mechanism—such as infection with a particular virus or strain of bacteria—is also necessary. In Sjogren's syndrome, the immune system first targets the moisture-secreting glands of the eyes and mouth. But it can also damage other parts of the body, such as the joints, thyroid, kidneys, liver, lungs, skin and nerves.

The most common complications of Sjogren's syndrome involve the eyes and mouth and include dental cavities, yeast infections of the mouth and vision problems. Less common complications may affect the lungs, kidneys or liver, unborn baby, lymph nodes or nerves.

Autoimmune Thyroiditis

In some embodiments, provided peptides are used in the treatment of autoimmune thyroiditis. Autoimmune thyroiditis, is a disease in which the body interprets the thyroid glands and its hormone products T3, T4 and TSH as threats, therefore producing special antibodies that target the thyroid's cells, thereby destroying it. It presents with hypothyroidism or hyperthyroidism and the presence or absence of goiters. Specialists clinically separate autoimmune thyroiditis into two categories. If goiters are present, it is understood as Hashimoto's Thyroiditis. On the other hand, if the thyroid is atrophic, but does not present goiters, it is denominated Atrophic Thyroiditis. If the symptoms of thyroiditis appear in women after giving birth, it is attributed to such and therefore called Postpartum Thyroiditis. The effects of this disease are not permanent but transient. Symptoms may come and go depending on whether the patient receives treatment, and whether the treatment is effective.

The symptoms for autoimmune thyroiditis may vary depending on whether it causes hyperthyroidism or hypothyroidism. Hyperthyroidism can cause sweating, rapid heart rate, anxiety, tremors, fatigue, difficulty sleeping, sudden weight loss, and protruding eyes. Hypothyroidism can cause weight gain, fatigue, dry skin, hair loss, intolerance to cold, and constipation.

The exact cause for autoimmune thyroiditis is not known for certain, but researchers have found high correlations with aspects such as genetics, high iodine consumption, and age. The disease is said to be inherited as a dominant trait because it has been reported that as many as fifty percent of the first degree relatives of patients with some type of autoimmune thyroiditis present thyroid antibodies in serum. Some studies have even related it to chromosome 21 because of its high correlation with patients with Down's syndrome and familial Alzheimer's disease. Still, this theory is doubted, since patients with Turner's syndrome also present a high prevalence of autoimmune thyroiditis (up to fifty percent). Autoimmune thyroiditis has a higher prevalence in societies that have a higher intake of iodine in their diet, such as the United States and Japan. Also, the rate of lymphositic infiltration increased in areas where the iodine intake was once low, but had been given iodine supplementation. When in the presence of excess iodine, the gland is unable to avoid its inhibitory effect on the biosynthesis of thyroid hormones. This is why when a person has excess iodine in his or her diet or is administered with additional supplementation in areas where sufficient iodine has been noted, it can induce reversible hypothyroidism. The mean age of prevalence in women is higher than in men by one year, 58 and 59 years old respectively. Autoimmune thyroiditis can also affect children. Although it is very rare for children under the age of five, it can occur, and it accounts for around 40 percent of the cases in adolescents with goiters. In the case of hypothyroidism, patients over the age of 45 have more chances of developing autoimmune thyroiditis.

Asthma

In some embodiments, provided peptides are used in the treatment of asthma. Asthma is a condition in which the airways narrow and swell and produce extra mucus. This can make breathing difficult and trigger coughing, wheezing and shortness of breath. For some people, asthma is a minor nuisance. For others, it can be a major problem that interferes with daily activities and may lead to a life-threatening asthma attack.

Asthma symptoms range from minor to severe and vary from person to person. A person may have infrequent asthma attacks, have symptoms only at certain times—such as when exercising—or have symptoms all the time. Asthma signs and symptoms include: shortness of breath, chest tightness or pain, trouble sleeping caused by shortness of breath, coughing or wheezing, a whistling or wheezing sound when exhaling (wheezing is a common sign of asthma in children), and coughing or wheezing attacks that are worsened by a respiratory virus, such as a cold or the flu. Signs that a person's asthma is probably worsening include: asthma signs and symptoms that are more frequent and bothersome, increasing difficulty breathing (measurable with a peak flow meter, a device used to check how well one's lungs are working), and the need to use a quick-relief inhaler more often. For some people, asthma symptoms flare up in certain situations. In exercise-induced asthma, symptoms may be worse when the air is cold and dry. In occupational asthma, symptoms mays triggered by workplace irritants such as chemical fumes, gases or dust. In allergy-induced asthma, symptoms may be triggered by particular allergens, such as pet dander, cockroaches or pollen.

Cancer

In some embodiments, provided peptides are used in the treatment of tumors or cancers (e.g., soft tissue or solid tumors), such as pancreatic cancer, leukemia (e.g., Hodgkin's lymphoma), glioblastoma, astrocytoma, lymphoma, melanoma or prostate cancer.

Pancreatic Cancer

Pancreatic cancer begins in the tissues of the pancreas—an organ in the abdomen that lies horizontally behind the lower part of the stomach. The pancreas secretes enzymes that aid digestion and hormones that help regulate the metabolism of sugars. Pancreatic cancer often has a poor prognosis, even when diagnosed early. Pancreatic cancer typically spreads rapidly and is seldom detected in its early stages, which is a major reason why it's a leading cause of cancer death. Signs and symptoms may not appear until pancreatic cancer is quite advanced and surgical removal isn't possible.

Signs and symptoms of pancreatic cancer often don't occur until the disease is advanced. When signs and symptoms do appear, they may include: upper abdominal pain that may radiate to the back, yellowing of the skin and the whites of the eyes (jaundice), loss of appetite, weight loss, depression, and blood clots. As pancreatic cancer progresses, it can cause complications such as: jaundice, pain, bowel obstruction, and weight loss.

The cause of pancreatic cancer is unclear. Pancreatic cancer occurs when cells in the pancreas develop mutations in their DNA. These mutations cause cells to grow uncontrollably and to continue living after normal cells would die. These accumulating cells can form a tumor. Most pancreatic cancer begins in the cells that line the ducts of the pancreas. This type of cancer is called pancreatic adenocarcinoma or pancreatic exocrine cancer. Rarely, cancer can form in the hormone-producing cells of the pancreas. This type of cancer is called islet cell cancer or pancreatic endocrine cancer.

Melanoma

In some embodiments, provided peptides are used in the treatment of inflammation associated with melanoma. Melanoma, the most serious type of skin cancer, develops in the cells (melanocytes) that produce melanin—the pigment that gives skin its color. Melanoma can also form in the eyes and, rarely, in internal organs, such as the intestines. The risk of melanoma seems to be increasing in people under 40, especially women. Knowing the warning signs of skin cancer can help ensure that cancerous changes are detected and treated before the cancer has spread. Melanoma can be treated successfully if it is detected early.

Melanomas can develop anywhere on the body. They most often develop in areas that have had exposure to the sun, such as the back, legs, arms and face. Melanomas can also occur in areas that don't receive much sun exposure, such as the soles of the feet, palms of the hands and fingernail beds. These hidden melanomas are more common in people with darker skin. The first melanoma signs and symptoms often are: a change in an existing mole and the development of a new pigmented or unusual-looking growth on the skin. Melanoma doesn't always begin as a mole. It can also occur on otherwise normal-appearing skin. Characteristics of unusual moles that may indicate melanomas or other skin cancers are: asymmetrical shape, irregular border, changes in color, diameter, and evolving. Other suspicious changes in a mole may include: scaliness, itching, spreading of pigment from the mole into the surrounding skin, and oozing or bleeding. Cancerous (malignant) moles vary greatly in appearance. Some may show all of the changes listed above, while others may have only one or two unusual characteristics. Melanomas can also develop in areas of the body that have little or no exposure to the sun, such as the spaces between toes and on the palms, soles, scalp or genitals. These are sometimes referred to as hidden melanomas, because they occur in places most people wouldn't think to check. When melanoma occurs in people with darker skin, it's more likely to occur in a hidden area. Hidden melanomas include: melanoma under a nail, melanoma in the mouth, digestive tract, urinary tract or vagina, and melanoma in the eye.

Melanoma occurs when something goes awry in the melanin-producing cells (melanocytes) that give skin its color. Normally, skin cells develop in a controlled and orderly way—healthy new cells push older cells toward the skin's surface, where they die and eventually fall off. But when some cells develop DNA damage, new cells may begin to grow out of control and can eventually form a mass of cancerous cells. Just what damages DNA in skin cells and how this leads to melanoma isn't clear. It's likely that a combination of factors, including environmental and genetic factors, causes melanoma. Still, doctors believe exposure to ultraviolet (UV) radiation from the sun and from tanning lamps and beds is the leading cause of melanoma. UV light doesn't cause all melanomas, especially those that occur in places on the body that don't receive exposure to sunlight. This indicates that other factors may contribute to the risk of melanoma.

Prostate Cancer

In some embodiments, provided peptides are used in the treatment of inflammation associated with prostate cancer. Prostate cancer is cancer that occurs in a man's prostate—a small walnut-shaped gland that produces the seminal fluid that nourishes and transports sperm. Prostate cancer is one of the most common types of cancer in men. Prostate cancer usually grows slowly and initially remains confined to the prostate gland, where it may not cause serious harm. While some types of prostate cancer grow slowly and may need minimal or no treatment, other types are aggressive and can spread quickly. Prostate cancer that is detected early—when it's still confined to the prostate gland—has a better chance of successful treatment. Prostate cancer may not cause signs or symptoms in its early stages. Prostate cancer that is more advanced may cause signs and symptoms such as: trouble urinating, decreased force in the stream of urine, blood in the urine, blood in the semen, general pain in the lower back, hips or thighs, discomfort in the pelvic area, bone pain, and erectile dysfunction. Complications of prostate cancer and its treatment include: metastasized cancer, incontinence and erectile dysfunction.

It's not clear what causes prostate cancer. Doctors know that prostate cancer begins when some cells in the prostate become abnormal. Mutations in the abnormal cells' DNA cause the cells to grow and divide more rapidly than normal cells do. The abnormal cells continue living, when other cells would die. The accumulating abnormal cells form a tumor that can grow to invade nearby tissue. Some abnormal cells can break off and spread (metastasize) to other parts of the body.

Transplant Rejection

In some embodiments, provided peptides are used in the treatment of transplant rejection (e.g. destruction of pancreatic islet cells in islet cell transplantation, delayed graft failure in kidney or other organ transplantation).

Destruction of Pancreatic Islet Cells in Islet Cell Transplantation

In some embodiments, provided peptides are used in the treatment of destruction of pancreatic islet cells in islet cell transplantation. The two types of pancreatic islet transplantation are allo-transplantation and auto-transplantation. Pancreatic islet allo-transplantation is a procedure in which islets from the pancreas of a deceased organ donor are purified, processed, and transferred into another person. Pancreatic islet allo-transplantation is currently labeled an experimental procedure until the transplantation technology is considered successful enough to be labeled therapeutic.

For each pancreatic islet allo-transplant infusion, researchers use specialized enzymes to remove islets from the pancreas of a single, deceased donor. The islets are purified and counted in a lab. Transplant patients typically receive two infusions with an average of 400,000 to 500,000 islets per infusion. Once implanted, the beta cells in these islets begin to make and release insulin. Pancreatic islet allo-transplantation is performed in certain patients with type 1 diabetes whose blood glucose levels are difficult to control. The goals of the transplant are to help these patients achieve normal blood glucose levels with or without daily injections of insulin and to reduce or eliminate hypoglycemia unawareness—a dangerous condition in which a person with diabetes cannot feel the symptoms of hypoglycemia, or low blood glucose. When a person feels the symptoms of hypoglycemia, steps can be taken to bring blood glucose levels back to normal.

Pancreatic islet allo-transplants are only performed at hospitals that have received permission from the U.S. Food and Drug Administration (FDA) for clinical research on islet transplantation. The transplants are often performed by a radiologist—a doctor who specializes in medical imaging. The radiologist uses x rays and ultrasound to guide the placement of a thin, flexible tube called a catheter through a small incision in the upper abdomen—the area between the chest and hips—and into the portal vein of the liver. The portal vein is the major vein that supplies blood to the liver. The islets are then infused, or pushed, slowly into the liver through the catheter. Usually, the patient receives a local anesthetic and a sedative. In some cases, a surgeon performs the transplant using general anesthesia. Patients often need two or more transplants to get enough functioning islets to stop or reduce their need for insulin injections.

Pancreatic islet auto-transplantation is performed following total pancreatectomy—the surgical removal of the whole pancreas—in patients with severe and chronic, or long lasting, pancreatitis that cannot be managed by other treatments. This procedure is not considered experimental. Patients with type 1 diabetes cannot receive pancreatic islet auto-transplantation. The procedure is performed in a hospital, and the patient receives general anesthesia. The surgeon first removes the pancreas and then extracts and purifies islets from the pancreas. Within hours, the islets are infused through a catheter into the patient's liver. The goal is to give the body enough healthy islets to make insulin.

As with any organ transplant, the recipient of an islet transplant must take drugs every day to keep the body from rejecting the islets. The immune system is programmed to destroy bacteria, viruses, and tissue it recognizes as "foreign," including transplanted islets. In addition, the autoimmune response that destroyed transplant recipients' own islets in the first place can recur and attack the transplanted islets.

Delayed Graft Failure in Kidney Transplantation

In some embodiments, provided peptides are used in the treatment of delayed graft failure in kidney transplantation. Delayed graft function is a form of acute renal failure resulting in post-transplantation oliguria, increased allograft immunogenicity and risk of acute rejection episodes, and decreased long-term survival. Factors related to the donor and prerenal, renal, or postrenal transplant factors related to the recipient can contribute to this condition. Experimental studies have demonstrated that both ischaemia and reinstitution of blood flow in ischaemically damaged kidneys after hypothermic preservation activate a complex sequence of events that sustain renal injury and play a pivotal part in the development of delayed graft function. Elucidation of the pathophysiology of renal ischaemia and reperfusion injury has contributed to the development of strategies to decrease the rate of delayed graft function, focusing on donor management, organ procurement and preservation techniques, recipient fluid management, and pharmacological agents (vasodilators, antioxidants, anti-inflammatory agents). Several new drugs show promise in animal studies in preventing or ameliorating ischaemia-reperfusion injury and possibly delayed graft function, but definitive clinical trials are lacking. The goal of monotherapy for the prevention or treatment of is perhaps unattainable, and multidrug approaches or single drug targeting multiple signals will be the next step to reduce post-transplantation injury and delayed graft function. Additional detail can be found in Perico et al, Lancet, 364(9447), pages 1814-27 (2004), the entire disclosure of which is hereby incorporated by reference.

Stroke

In some embodiments, provided peptides are used in the treatment of stroke. A stroke occurs when the blood supply to part of the brain is interrupted or severely reduced, depriving brain tissue of oxygen and nutrients. Within minutes, brain cells begin to die.

It is important to note when signs and symptoms of a stroke begin because the length of time they have been present may guide treatment decisions. Signs and symptoms of stroke include: trouble with walking, trouble with speaking and understanding, paralysis or numbness of the face, arm or leg, trouble with seeing in one or both eyes, and headache. A stroke can sometimes cause temporary or permanent disabilities, depending on how long the brain suffers a lack of blood flow and which part was affected.

Complications may include: paralysis or loss of muscle movement, difficulty talking or swallowing, memory loss or thinking difficulties, emotional problems, pain, and changes in behavior and self-care.

A stroke occurs when the blood supply to the brain is interrupted or reduced. This deprives the brain of oxygen and nutrients, which can cause brain cells to die. A stroke may be caused by a blocked artery (ischemic stroke) or a leaking or burst blood vessel (hemorrhagic stroke). Some people may experience a temporary disruption of blood flow through their brain (transient ischemic attack). The majority of strokes are ischemic strokes. Ischemic strokes occur when the arteries to the brain become narrowed or blocked, causing severely reduced blood flow (ischemia). The most common ischemic strokes include: thrombotic stroke (blood clot in one the arteries that supply blood to the brain) and embolic stroke (blood clot or other debris forms away from the brain—commonly in the heart—and travels through the bloodstream to lodge in a narrow brain artery).

Hemorrhagic stroke occurs when a blood vessel in the brain leaks or ruptures. Brain hemorrhages can result from many conditions that affect the blood vessels, including uncontrolled high blood pressure (hypertension) and weak spots in blood vessel walls (aneurysms). A less common cause of hemorrhage is the rupture of an arteriovenous malformation (AVM)—an abnormal tangle of thin-walled blood vessels, present at birth. The types of hemorrhagic stroke include: intracerebral hemorrhage (blood vessel in brain bursts and spills into surrounding brain tissue, damaging brain cells) and subarachnoid hemorrhage (artery on or near the surface of the brain bursts and spills into the space between the brain and the skull).

A transient ischemic attack (TIA)—also called a ministroke—is a brief episode of symptoms similar to those one would have in a stroke. A transient ischemic attack is caused by a temporary decrease in blood supply to part of the brain. TIAs often last less than five minutes. Like an ischemic stroke, a TIA occurs when a clot or debris blocks blood flow to part of the brain. A TIA doesn't leave lasting symptoms because the blockage is temporary.

Neurodegenerative Diseases

In some embodiments, provided peptides are used in the treatment or prevention of neuronal death. In some embodiments, neuronal death is associated with a neurodegenerative disease including, but not limited to, amyotrophic lateral sclerosis (ALS), Huntington's disease, Alzheimer's disease, Parkinson's disease, multiple sclerosis, vascular cognitive impairment (VCI).

Amyotrophic Lateral Sclerosis (ALS)

In some embodiments, provided peptides are used in the treatment of inflammation associated with amyotrophic lateral sclerosis (ALS). ALS is a serious neurological disease that causes muscle weakness, disability and eventually death. ALS is often called Lou Gehrig's disease, after the famous baseball player who was diagnosed with it in 1939. In the U.S., ALS and motor neuron disease (MND) are sometimes used interchangeably. Worldwide, ALS occurs in 1 to 3 people per 100,000. In the vast majority of cases—90 to 95 percent—doctors don't yet know why ALS occurs. About 5 to 10 percent of ALS cases are inherited.

Early signs and symptoms of ALS include: difficulty lifting the front part of the foot and toes (footdrop), weakness in the leg, feet or ankles, hand weakness or clumsiness, slurring of speech or trouble swallowing, and muscle cramps and twitching in the arms, shoulders and tongue. The disease frequently begins in the hands, feet or limbs, and then spreads to other parts of the body. As the disease advances, the muscles become progressively weaker until they're paralyzed. It eventually affects chewing, swallowing, speaking and breathing.

In ALS, the nerve cells that control the movement of the muscles gradually die, so the muscles progressively weaken and begin to waste away. Up to 1 in 10 cases of ALS is inherited. But the remainder appear to occur randomly. Researchers are studying several possible causes of ALS, including: genetic mutations, chemical imbalances, disorganized immune response and mishandled proteins within neurons.

Huntington's Disease

In some embodiments, provided peptides are used in the treatment of inflammation associated with Huntington's disease. Huntington's disease is an inherited disease that causes the progressive breakdown (degeneration) of nerve cells in the brain. Huntington's disease has a broad impact on a person's functional abilities and usually results in movement, thinking (cognitive) and psychiatric disorders. Most people with Huntington's disease develop signs and symptoms in their 40s or 50s, but the onset of disease may be earlier or later in life. When disease onset begins before age 20, the condition is called juvenile Huntington's disease. Earlier onset often results in a somewhat different presentation of symptoms and faster disease progression.

Huntington's disease usually causes movement, cognitive and psychiatric disorders with a wide spectrum of signs and symptoms. Which symptoms appear first varies greatly among affected people. During the course of the disease, some disorders appear to be more dominant or have a greater effect on functional ability. The movement disorders associated with Huntington's disease can include both involuntary movements and impairments in voluntary movements: involuntary jerking or writhing movements (chorea), involuntary, sustained contracture of muscles (dystonia), muscle rigidity, slow, uncoordinated fine movements, slow or abnormal eye movements, impaired gait, posture and balance, difficulty with the physical production of speech, and difficulty swallowing. Impairments in voluntary movements— rather than the involuntary movements—may have a greater impact on a person's ability to work, perform daily activities, communicate and remain independent.

Cognitive impairments often associated with Huntington's disease include: difficulty planning, organizing and prioritizing tasks, inability to start a task or conversation, lack of flexibility, or the tendency to get stuck on a thought, behavior or action (perseveration), lack of impulse control that can result in outbursts, acting without thinking and sexual promiscuity, problems with spatial perception that can result in falls, clumsiness or accidents, lack of awareness of one's own behaviors and abilities, difficulty focusing on a task for long periods, slowness in processing thoughts or "finding" words, and difficulty in learning new information The most common psychiatric disorder associated with Huntington's disease is depression. This isn't simply a reaction to receiving a diagnosis of Huntington's disease. Instead, depression appears to occur because of injury to the brain and subsequent changes in brain function. Signs and symptoms may include: feelings of sadness or unhappiness, loss of interest in normal activities, social withdrawal, insomnia or excessive sleeping, fatigue, tiredness and loss of energy, feelings of worthlessness or guilt, indecisiveness, distractibility and decreased concentration, frequent thoughts of death, dying or suicide, changes in appetite, and reduced sex drive. Other changes in mood or personality, but not necessarily specific psychiatric disorders, may include: irritability, apathy, anxiety, and sexual inhibition or inappropriate sexual behaviors.

The onset and progression of Huntington's disease in younger people may be slightly different from that in adults. Problems that often present themselves early in the course of the disease include: loss of previously learned academic or physical skills, rapid, significant drop in overall school performance, behavioral problems, contracted and rigid muscles that affect gait (especially in young children), changes in fine motor skills that might be noticeable in skills such as handwriting, tremors or slight involuntary movements, and seizures.

After the onset of Huntington's disease, a person's functional abilities gradually worsen over time. The rate of disease progression and duration varies. The time from disease onset to death is often about 10 to 30 years. Juvenile onset usually results in death in fewer than 15 years. The clinical depression associated with Huntington's disease may increase the risk of suicide. Some research suggests that the greater risk of suicide occurs before a diagnosis is made and in middle stages of the disease when a person has begun to lose independence. Eventually, a person with Huntington's disease requires help with all activities of daily living and care. Late in the disease, he or she will likely be confined to a bed and unable to speak. However, a person's understanding of surroundings and interactions remain intact for a long time. Common causes of death include: pneumonia or other infections, injuries related to falls, and complications related to the inability to swallow.

Huntington's disease is caused by an inherited defect in a single gene. Huntington's disease is an autosomal dominant disorder, which means that a person needs only one copy of the defective gene to develop the disorder. With the exception of genes on the sex chromosomes, a person inherits two copies of every gene—one copy from each parent. A parent with a defective Huntington gene could pass along the defective copy of the gene or the healthy copy. Each child in the family, therefore, has a 50 percent chance of inheriting the gene that causes the genetic disorder.

Parkinson's Disease

In some embodiments, provided peptides are used in the treatment of Parkinson's disease. Parkinson's disease is a progressive disorder of the nervous system that affects movement. It develops gradually, sometimes starting with a barely noticeable tremor in just one hand. But while tremor may be the most well-known sign of Parkinson's disease, the disorder also commonly causes stiffness or slowing of movement.

Parkinson's disease symptoms and signs may vary from person to person. Early signs may be mild and may go unnoticed. Symptoms often begin on one side of the body and usually remain worse on that side, even after symptoms begin to affect both sides. Parkinson's signs and symptoms may include: tremor, slowed movement (bradykinesia), rigid muscles, impaired posture and balance, loss of automatic movements, speech changes, and writing changes. Parkinson's disease is often accompanied by these additional problems, which are variably treatable: thinking difficulties, depression and emotional changes, sleep problems and disorders, bladder problems, constipation, and sexual dysfunction.

The cause of Parkinson's disease is unknown, but several factors appear to play a role, including: a person's genes and environmental triggers. Many changes occur in the brains of people with Parkinson's disease, including: clumps of specific substances called Lewy bodies within brain cells, which are microscopic markers of Parkinson's disease, and a clumped form of the protein alpha-synuclein that is found in Lewy bodies and can't be broken down by cells.

Vascular Cognitive Impairment (VCI)

In some embodiments, provided peptides are used in the treatment of vascular cognitive impairment (VCI). Vascular cognitive impairment (VCI) is a spectrum of cognitive impairments caused by various types of cerebrovascular disease that occurs as a result of interaction between a variety of vascular risk factors such as hypertension, obesity, dyslipidemia, diabetes mellitus, stroke and silent stroke. Included in this spectrum is Vascular Dementia (VaD), (the second leading cause of dementia after Alzheimer's disease (AD)) and Mild Vascular Cognitive Impairment (MVCI).

VCI may result from clinical stroke of the large vessels or from microangiopathic changes in the small cerebral vessels. Radiological findings might include abnormally bright spots on a T2 weighted MRI scan in periventricular regions or in the deep white matter. This so-called "white matter disease" is commonly associated with vascular risk factors such as smoking and hypertension, and with subtle decline in cognitive performance with aging. Brain MRI might also show "lacunar infarcts" (spots which are hypointense on a T1 MRI scan) which are indicative of small "silent strokes", or hemorrhagic findings (small hemorrhagic findings are often referred to as "microbleeds"). The relative importance and precise etiology of these findings remains a subject of debate. 0Cognitive domains commonly affected by VCI include psychomotor processing speed, executive function and verbal memory.

Traumatic Brain Injury (TBI)

In some embodiments, provided peptides are used in the treatment of traumatic brain injury (TBI). TBI occurs when an external mechanical force causes brain dysfunction. Traumatic brain injury usually results from a violent blow or jolt to the head or body. An object penetrating the skull, such as a bullet or shattered piece of skull, also can cause traumatic brain injury.

Traumatic brain injury can have wide-ranging physical and psychological effects. Some signs or symptoms may appear immediately after the traumatic event, while others may appear days or weeks later. The signs and symptoms of mild traumatic brain injury may include: loss of consciousness for a few seconds to a few minutes, no loss of consciousness, but a state of being dazed, confused or disoriented, memory or concentration problems, headache, dizziness or loss of balance, nausea or vomiting, sensory problems, such as blurred vision, ringing in the ears or a bad taste in the mouth, sensitivity to light or sound, mood changes or mood swings, feeling depressed or anxious, fatigue or drowsiness, difficulty sleeping, and sleeping more than usual.

Moderate to severe traumatic brain injuries can include any of the signs and symptoms of mild injury, as well as the following symptoms that may appear within the first hours to days after a head injury: loss of consciousness from several minutes to hours, profound confusion, agitation, combativeness or other unusual behavior, slurred speech, inability to awaken from sleep, weakness or numbness in fingers and toes, loss of coordination, persistent headache or headache that worsens, repeated vomiting or nausea, convulsions or seizures, dilation of one or both pupils of the eyes, and clear fluids draining from the nose or ears.

Infants and young children with brain injuries may lack the communication skills to report headaches, sensory problems, confusion and similar symptoms. In a child with traumatic brain injury, the following signs and symptoms may be observed: change in eating or nursing habits, persistent crying and inability to be consoled, unusual or easy irritability, change in ability to pay attention, change in sleep habits, sad or depressed mood, and loss of interest in favorite toys or activities.

Several complications can occur immediately or soon after a traumatic brain injury. Severe injuries increase the risk of a greater number of complications and more-severe complications. Complications associated with TBI include: altered consciousness (including coma, vegetative state, minimally conscious state, and locked-in syndrome). Some people with TBI will have seizures within the first week. Some serious injuries may result in recurring seizures, called post-traumatic epilepsy. Additionally, cerebrospinal fluid may build up in the spaces in the brain (cerebral ventricles) of some people who have had traumatic brain injuries, causing swelling and increased pressure in the brain. Skull fractures or penetrating wounds can tear the layers of protective tissues (meninges) that surround the brain. This can enable bacteria to enter the brain and cause infections. An infection of the meninges (meningitis) could spread to the rest of the nervous system if not treated. Several small or large blood vessels in the brain may be damaged in a traumatic brain injury. This damage could lead to a stroke, blood clots or other problems. Injuries to the base of the skull can damage nerves that emerge directly from the brain (cranial nerves). Cranial nerve damage may result in: paralysis of facial muscles, damage to the nerves responsible for eye movements, which can cause double vision, damage to the nerves that provide sense of smell, loss of vision, loss of facial sensation, and swallowing problems.

Most people who have had a significant brain injury will experience changes in their cognitive skills. TBI can result in problems with many skills, including: memory, learning, reasoning, problem solving, speed of mental processing, judgment, attention or concentration, multitasking, organization, decision making, beginning or completing tasks, and communication problems. Language and communications problems are common following TBI. These problems can cause frustration, conflict and misunderstanding for people with a TBI, as well as family members, friends and care providers. Communication problems may include: difficulty understanding speech or writing, difficulty speaking or writing, difficulty deciphering nonverbal signals, inability to organize thoughts and ideas, inability to use the muscles needed to form words (dysarthria), problems with changes in tone, pitch or emphasis to express emotions, attitudes or subtle differences in meaning, trouble starting or stopping conversations, trouble with turn taking or topic selection, trouble reading cues from listeners, and trouble following conversations.

People who've experienced brain injury often experience changes in behaviors. These may include: difficulty with self-control, lack of awareness of abilities, risky behavior, inaccurate self-image, difficulty in social situations, and verbal or physical outbursts. Emotional changes may include: depression, anxiety, mood swings, irritability, lack of empathy for others, anger, insomnia, and changes in self-esteem. Problems involving senses may include: persistent ringing in the ears, difficulty recognizing objects, impaired hand-eye coordination, blind spots or double vision, a bitter taste or a bad smell, skin tingling, pain or itching, and trouble with balance or dizziness. A TBI may increase the risk of diseases that result in the gradual degeneration of brain cells and gradual loss of brain functions. These include: Alzheimer's disease, Parkinson's disease, and dementia pugilistica.

Traumatic brain injury is caused by a blow or other traumatic injury to the head or body. The degree of damage can depend on several factors, including the nature of the event and the force of impact. Injury may include one or more of the following factors: damage to brain cells may be limited to the area directly below the point of impact on the skull, a severe blow or jolt can cause multiple points of damage because the brain may move back and forth in the skull, a severe rotational or spinning jolt can cause the tearing of cellular structures, a blast, as from an explosive device, can cause widespread damage, an object penetrating the skull can cause severe, irreparable damage to brain cells, blood vessels and protective tissues around the brain, and bleeding in or around the brain, swelling, and blood clots can disrupt the oxygen supply to the brain and cause wider damage. Common events causing traumatic brain injury include the following: falls, vehicle-related collisions, violence, sports injuries and explosive blasts and other combat injuries.

Pharmaceutical Compositions

In accordance with the methods of the invention, provided peptides as described herein can be administered to a subject alone (e.g., as a purified peptide or compound), or as a component of a composition or medicament (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration, for example intravenous or subcutaneous administration. Methods of formulating compositions are known in the art (see, e.g., Remington's Pharmaceuticals Sciences, 17th Edition, Mack Publishing Co., (Alfonso R. Gennaro, editor) (1989)). In some embodiments, a composition may comprise one or more liposomes, nanoparticles, and/or sterile aqueous or non-aqueous solutions, suspensions, and emulsions.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. A composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings.

For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

Provided peptides as described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Dosing

In some embodiments, a provided peptides and/or compositions are administered in a therapeutically effective amount and/or according to a dosing regimen that is correlated with a particular desired outcome (e.g., with treating or reducing risk for disease).

Any provided peptide as described herein (or a composition or medicament containing provided peptides as described herein) may be administered by any appropriate route. In some embodiments, provided peptides as described herein is administered intravenously. In some embodiments, provided peptides as described herein is administered subcutaneously. As used herein, the term "subcutaneous tissue" is defined as a layer of loose, irregular connective tissue immediately beneath the skin. For example, the subcutaneous administration may be performed by injecting a composition into areas including, but not limited to, thigh region, abdominal region, gluteal region, or scapular region. In other embodiments, provided peptides as described herein is administered by direct administration to a target tissue, such as heart or muscle (e.g., intramuscular), tumor (intratumorally), nervous system (e.g., direct injection into the brain; intraventricularly; intrathecally), or other target tissue such as the liver, kidney, etc. Alternatively, provided peptides as described herein (or a composition or medicament containing a peptide described herein) can be administered via inhalation, intraperitoneally, parenterally, intradermally, transdermally, or transmucosally (e.g., orally or nasally). More than one route can be used concurrently, if desired.

In some embodiments, provided peptides and/or compositions are administered in a therapeutically effective amount and/or according to a dosing regimen that is correlated with a particular desired outcome (e.g., with treating or reducing risk for disease).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce one or more symptoms by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. Alternatively or additionally, in some embodiments, an appropriate dose or amount is determined through use of one or more in vitro or in vivo assays to help identify desirable or optimal dosage ranges or amounts to be administered.

In various embodiments, provided peptides, or a composition comprising such peptides, is administered at a therapeutically effective amount. As used herein, the term "therapeutically effective amount" or "therapeutically effective dosage amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

Therapeutically effective dosage amounts of provided peptides, including derivatives, analogs, and/or salts thereof, may be present in varying amounts in various embodiments. In some embodiments, a therapeutically effective dosage amount can be, for example, about 1-10,000 µg/kg, about 5-1,500 µg/kg, about 100-1,000 µg/kg, or 50-500 µg/kg. In some embodiments, the therapeutically effective dosage amount can be, for example, about 1 µg/kg, 2.5 µg/kg, 5 µg/kg, 10 µg/kg, 20 µg/kg, 30 µg/kg, 40 µg/kg, 50 µg/kg, 60 mg/kg, 70 µg/kg, 80 µg/kg, 90 µg/kg, 100 µg/kg, 150 µg/kg, 200 µg/kg, 250 µg/kg, 300 µg/kg, 400 µg/kg, 500 µg/kg, 600 µg/kg, 700 µg/kg, 800 µg/kg, 900 µg/kg, 1000 µg/kg, or 1500 µg/kg. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.001 mg/kg weight to about 1 mg/kg weight, e.g. from about 0.001 mg/kg weight to about 0.9 mg/kg weight, from about 0.001 mg/kg weight to about 0.8 mg/kg weight, from about 0.001 mg/kg weight to about 0.8 mg/kg weight, from about 0.001 mg/kg weight to about 0.7 mg/kg weight, from about 0.001 mg/kg weight to about 0.6 mg/kg weight, from about 0.001 mg/kg weight to about 0.5 mg/kg weight, from about 0.01 mg/kg weight to about 1 mg/kg weight, from about 0.01 mg/kg weight to about 0.9 mg/kg weight, from about 0.01 mg/kg weight to about 0.8 mg/kg weight, from about 0.01 mg/kg weight to about 0.7 mg/kg weight, from about 0.01 mg/kg weight to about 0.6 mg/kg weight, from about 0.01 mg/kg weight to about 0.5 mg/kg weight, from about 0.02 mg/kg weight to about 1 mg/kg weight, from about 0.02 mg/kg weight to about 0.9 mg/kg weight, from about 0.02 mg/kg weight to about 0.8 mg/kg weight, from about 0.02 mg/kg weight to about 0.7 mg/kg weight, from about 0.02 mg/kg weight to about 0.6 mg/kg weight, from about 0.02 mg/kg weight to about 0.5 mg/kg weight, from about 0.03 mg/kg weight to about 1 mg/kg weight, from about 0.03 mg/kg weight to about 0.9 mg/kg weight, from about 0.03 mg/kg weight to about 0.8 mg/kg weight, from about 0.03 mg/kg weight to about 0.7 mg/kg weight, from about 0.03 mg/kg weight to about 0.6 mg/kg weight, from about 0.03 mg/kg weight to about 0.5 mg/kg weight, from about 0.04 mg/kg weight to about 1 mg/kg weight, from about 0.04 mg/kg weight to about 0.9 mg/kg weight, from about 0.04 mg/kg weight to about 0.8 mg/kg weight, from about 0.04 mg/kg weight to about 0.7 mg/kg weight, from about 0.04 mg/kg weight to about 0.6 mg/kg weight, from about 0.04 mg/kg weight to about 0.5 mg/kg weight, from about 0.05 mg/kg weight to about 1 mg/kg weight, from about 0.05 mg/kg weight to about 0.9 mg/kg weight, from about 0.05 mg/kg weight to about 0.8 mg/kg weight, from about 0.05 mg/kg weight to about 0.7 mg/kg weight, from about 0.05 mg/kg weight to about 0.6 mg/kg weight, from about 0.05 mg/kg weight to about 0.5 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In some embodiments, the provided peptides, and/or a composition comprising such peptides, is administered at an effective dose ranging from about 1-1,000 μg/kg/day (e.g., ranging from about 1-900 μg/kg/day, 1-800 μg/kg/day, 1-700 μg/kg/day, 1-600 μg/kg/day, 1-500 μg/kg/day, 1-400 μg/kg/day, 1-300 μg/kg/day, 1-200 μg/kg/day, 1-100 μg/kg/day, 1-90 μg/kg/day, 1-80 μg/kg/day, 1-70 μg/kg/day, 1-60 μg/kg/day, 1-50 μg/kg/day, 1-40 μg/kg/day, 1-30 μg/kg/day, 1-20 μg/kg/day, 1-10 μg/kg/day). In some embodiments, the provided peptides, and/or a composition comprising such peptides, are administered at an effective dose ranging from about 1-500 μg/kg/day. In some embodiments, the provided peptides, and/or a composition comprising such peptides, are administered at an effective dose ranging from about 50-500 μg/kg/day. In some embodiments, the provided peptides, and/or a composition comprising such peptides, are administered at an effective dose ranging from about 1-100 μg/kg/day. In some embodiments, the provided peptides, and/or a composition comprising such peptides, are administered at an effective dose ranging from about 1-60 μg/kg/day. In some embodiments, the provided peptides, and/or a composition comprising such peptides, are administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 μg/kg/day. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In some embodiments, In some embodiments, the provided peptides, and/or a composition comprising such peptides, are administered at an effective dose from about 1-1,000 pg/kg/day (e.g., ranging from about 1-900 pg/kg/day, 1-800 pg/kg/day, 1-700 pg/kg/day, 1-600 pg/kg/day, 1-500 pg/kg/day, 1-400 pg/kg/day, 1-300 pg/kg/day, 1-200 pg/kg/day, 1-100 pg/kg/day, 1-90 pg/kg/day, 1-80 pg/kg/day, 1-70 pg/kg/day, 1-60 pg/kg/day, 1-50 pg/kg/day, 1-40 pg/kg/day, 1-30 pg/kg/day, 1-20 pg/kg/day, 1-10 pg/kg/day). In some embodiments, the provided peptides, and/or a composition comprising such peptides, are administered at an effective dose ranging from about 1-60 μg/kg/day. In some embodiments, the provided peptides, and/or a composition comprising such peptides, are administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 pg/kg/day. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In some embodiments, a composition is provided as a pharmaceutical formulation. In some embodiments, a pharmaceutical formulation is or comprises a unit dose amount for administration in accordance with a dosing regimen correlated with achievement of the reduced incidence or risk of disease.

In some embodiments, a formulation comprising provided peptides as described herein is administered as a single dose. In some embodiments, a formulation comprising provided peptides as described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising provided peptides as described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising provided peptides as described herein is administered at regular intervals indefinitely. In some embodiments, a formulation comprising provided peptides as described herein is administered at regular intervals for a defined period. In some embodiments, a formulation comprising provided peptides as described herein is administered at regular intervals for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

Combination Therapies

In some embodiments, the provided peptides, and/or a composition comprising such peptides, may be administered in combination with one or more known therapeutic agents currently used for prophylaxis and treatment of diseases, disorders and conditions in which a CXCR mediated pathway is implicated (e.g. inflammation, stroke, traumatic brain injury, pancreatic cancer, and neurodegenerative diseases). These agents include anti-inflammatory agents, anticancer agents, neuroprotective agents, thrombolytic agents, immunosuppressants, antioxidants, α- or β-adrenergic agonist or antagonist or a NMDA receptor antagonist, all well known in the art.

Anti-inflammatory drugs or agents which may be coadministered with compounds according to the present invention include at least one agent such as a non-steroidal anti-inflammatory drug (NSAID), for example aspirin, ibuprofen, naproxen, an IMSAID such as PHE-GLU-GLY (FEG) or D-isomeric feG, a bioactive compound such as plumbagin or plumericin, or any one or more supplement including hyssop, ginger, tumeric, willow bark, hyperforin, omega-3 fatty acids and ginger, among others.

Anticancer agents which may be used in combination with compounds according to the present invention include, for example, microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes, among others. These may be selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, and mixtures thereof, among others.

Neuroprotective agents which may be used in combination with compounds according to the present invention include for example, dilostazol, desflurane, eldepryl, felbamate, felbatol, gagitril, latanoprost, methylprednisolone, modafinil, pergolide, permaqx, phentermine and topiramate (combination), pletal, provigil, osymia, rilutek, riluzole, selegiline, supreme, tiagabine, topamax, topiramate and xalatan, among others.

Thrombolytic agents which may be used in combination with compounds according to the present invention include, for example, abbokinase, activase, alteplase, cathflo activase, kinlytic, retavase, reteplase, tenecteplase, tnkase and urokinase, among others.

Immunosuppressant agents which may be used in combination with compounds according to the present invention include, for example, corticosteroids (e.g. prednisolone), ciclosporin (cyclosporine), tacrolimus, and cytotoxic agents (e.g. azathioprine, chlorambucil, cyclophosphamide, methotrexate), among others.

Antioxidants which may be used in combination with compounds according to the present invention include, for example, Glutathione, vitamin C, vitamin A, vitamin E, catalase, superoxide dismutase, peroxidases, among numerous others.

Other compounds which may be used in combination with compounds according to the present invention include α- or β-adrenergic agonist or antagonist or a NMDA receptor antagonist, all well known in the art.

In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

The invention will be more fully understood by reference to the following examples. They should not, however, be construed as limiting the scope of the invention. All literature citations are incorporated by reference.

EXEMPLIFICATION

The following examples demonstrate, among other things, the CXCR2 antagonism and neuroprotective properties of provided peptides (e.g., ac-PGG) in various embodiments and are not intended to limit the present claims.

Example 1—Ac-PGG is an Antagonist of CXCR2 Receptor

This Example shows, among other things, that administration of ac-PGG peptide results in effects antagonistic to those of effects of ac-PGP mediated by the CXCR2 receptor. These results are particularly surprising since ac-PGG was previously thought to be an inert control peptide with no biological function, and certainly not a potential therapeutic action.

First, the mechanism by which ac-PGP induces apoptosis in cortical neurons was investigated. Because ac-PGP is reported to engage neutrophil CXCR2 receptors, whether an established CXCR2 receptor antagonist, SB225002, could influence ac-PGP neurotoxicity was tested.

Primary Cortical Neuron Culture

Cortical neurons were obtained from Sprague-Dawley rat embryos at day 18 of gestation. Cortices were triturated digested with 0.025% trypsin in phosphate buffer saline (PBS) for 10 minutes. Digestion was stopped by the addition of Dulbecco's Modified Eagle Medium (DMEM) containing 10% fetal bovine serum (FBS). Trypsinized cells were filtered using 70 μM disposable cell filters (Becton-Dickinson), washed twice with Neurobasal medium (Gibco) containing 4% FBS, and preplated 4 times for 30 minutes in 150 mm vacuum-plasma treated dishes (Becton-Dickinson). During these preplating steps, primarily non-neuronal cells adhere to the dish, thereby enriching the neuronal population. Enriched neurons were plated at a density of 50×103/cm2 in Neurobasal medium containing 4% FBS, 25 μM Glutamax (Gibco), and penicillin-streptomycin (Gibco) in white clear-bottomed 96-well plates (353377) or 24-well plates (353226) (Becton-Dickinson) coated overnight with 50 μg/ml poly-D-lysine. At plating, spaces between wells in 96-well plates were filled with 50 μl sterile water to minimize evaporation of medium at the edges of the dish. Twenty-four hours later (1 day in vitro, 1 DIV), 50% of the medium was replaced with Neurobasal medium, 2% B27 (Gibco), and 4 μM cytosine arabinoside (AraC) (2 μM AraC final). At 5 DIV, 50% of the medium was replaced with Neurobasal, 2% B27. At 7 DIV, cortical cultures were 98% neurons as assessed by microtubule-associated protein 2 (MAP2) antibody labeling and flow cytometry analysis (data not shown).

Oxygen-Glucose Deprivation (OGD)

Cortical neurons were deprived of oxygen and glucose by incubation in deoxygenated glucose-free Hank's buffered saline solution (HBSS). HBSS was prepared as follows: sodium chloride, NaCl, 8.0 g/L, potassium chloride, KCl, 0.4 g/L, potassium phosphate monobasic, KH2PO4, 0.06 g/L, sodium phosphate dibasic, Na2HPO4, 0.048 g/L, magnesium sulfate, MgSO4, 0.098 g/L, calcium chloride, CaCl2, 0.14 g/L, sodium bicarbonate, NaHCO3, 0.35 g/L, D-glucose, C6H12O6, 1.0 g/L. Solutions were adjusted to pH 7.4 and sterilized by vacuum filtration through 0.2 μm polyether sulfone (PES) membranes. Glucose-free HBSS was prepared by omitting glucose and adding an additional half molar amount of NaCl to adjust osmolarity (8.162 g/L NaCl). Glucose-free HBSS was deoxygenated in a gas washing bottle with 95% nitrogen, 5% CO2 for 20 minutes at a flow rate of 3 L/min in a 37° C. water bath. Culture dishes were washed twice with deoxygenated glucose-free HBSS and incubated for 2 hours in glucose-free deoxygenated HBSS (OGD). Normoxic control cells were handled identically but were incubated in a 5% CO2 incubator with normal HBSS pre-equilibrated in a 5% CO2 atmosphere overnight.

Results

Figure 1B:
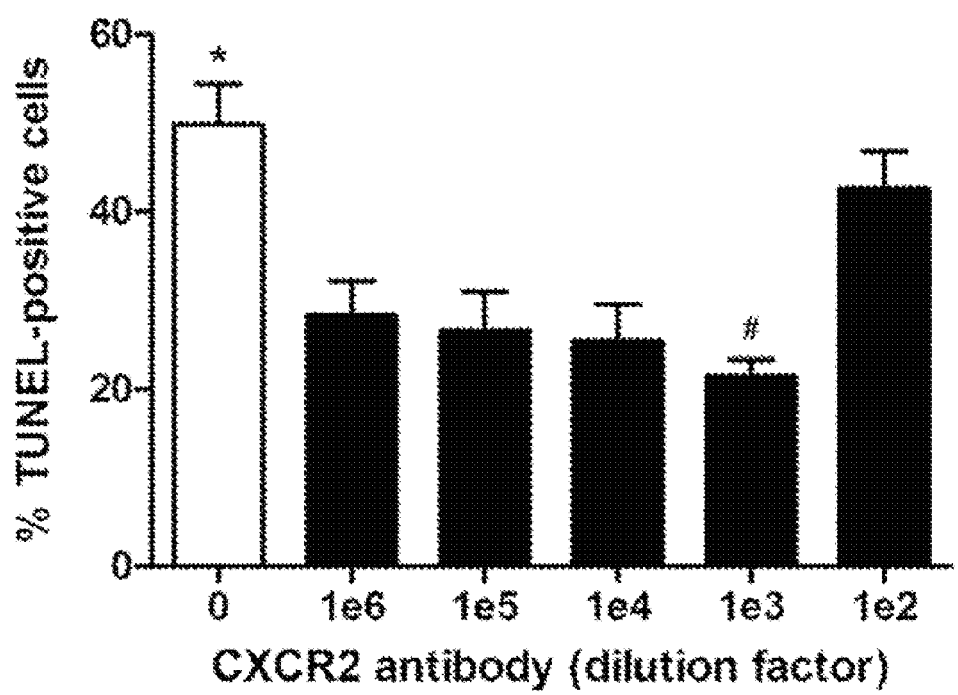
Figure 1C:
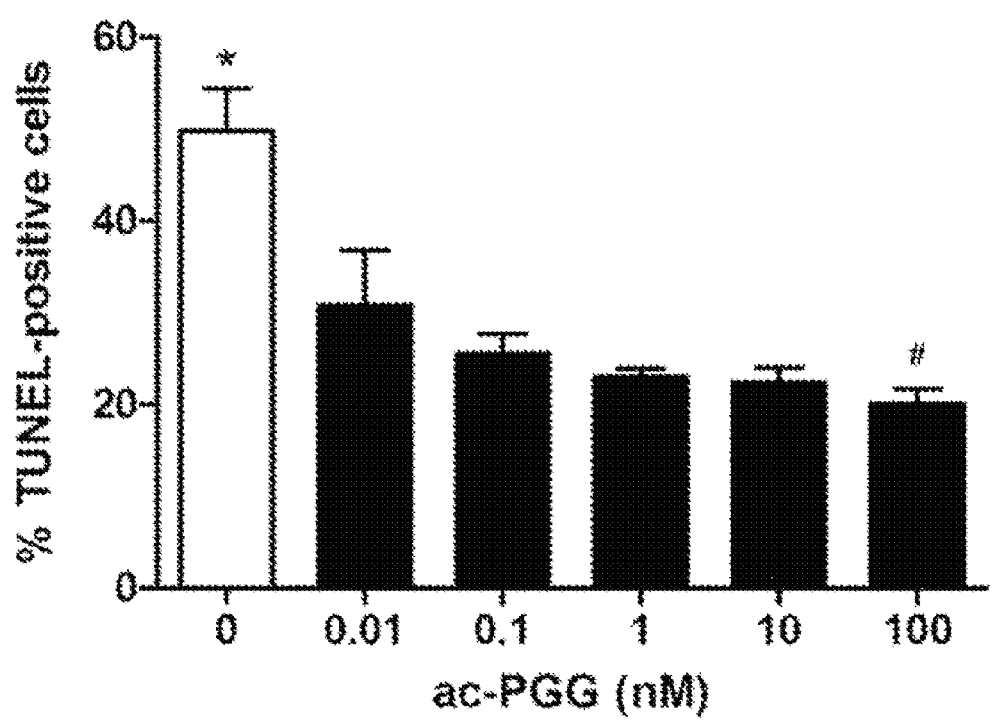

It was found that low nanomolar concentrations of SB225002 blocked ac-PGP neurotoxicity as measured via TUNEL stain (FIG. 1 A). These results indicate that ac-PGP-induced apoptosis is CXCR2 receptor-dependent in cortical neurons. To further confirm the involvement of CXCR2 receptors in ac-PGP mediated neurotoxicity, primary neurons were incubated with an antibody against the CXCR2 receptor extracellular ligand binding domain prior to ac-PGP exposure. A 1:1000 dilution of the antibody blocked ac-PGP-induced apoptosis (FIG. 1 B). Together, these results indicate that ac-PGP initiates neuronal apoptosis through its binding at neuronal CXCR2 receptors. Pretreatment of neurons with ac-PGG (FIG. 1 C) resulted in significant neuroprotection against ac-PGP exposure similar to that observed with established CXCR2 antagonists. These results indicate, for the first time, that ac-PGG is a potent CXCR2 antagonist when present in concentrations as much as 1000 times below the concentration of a CXCR2 ligand.

Figure 2:
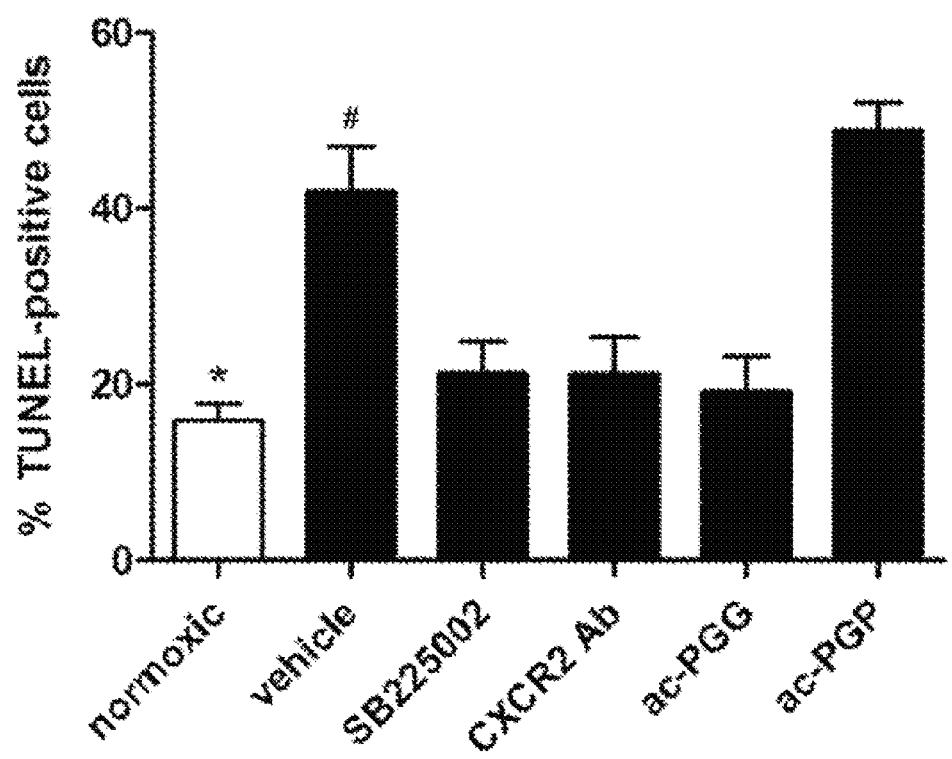
FIG. 2 depicts an exemplary graph showing the effects of pretreatment with vehicle, SB225002, CXCR2 antibody, ac-PGG or ac-PGP on neurons subjected to 2-hour oxygen-glucose deprivation (OGD). Significant apoptosis was induced in vehicle- and ac-PGP treated neurons compared to normoxic controls (*). Neurons pretreated with SB225002, CXCR2 antibody, or ac-PGG were significantly less apoptotic than vehicle-treated controls (#).

To investigate the possible involvement of ac-PGP and CXCR2 receptors in neuronal death after ischemia/reperfusion, an oxygen-glucose deprivation (OGD) model of stroke in primary neurons was used. Two-hour OGD followed by 24-hour reoxygenation resulted in roughly 40% apoptotic cell death (FIG. 2). Pretreatment with the CXCR2 antagonist SB225002, a CXCR2 antibody, or ac-PGG peptide each resulted in significant protection from OGD. These results indicate a major role for CXCR2 receptor binding in neuronal toxicity after ischemia. Treatment with ac-PGP during OGD resulted in only slightly higher apoptosis than OGD alone. The lack of an additive effect of OGD and ac-PGP treatment, together with the near complete protection of neurons afforded by CXCR2 blockade, suggests that CXCR2 receptor binding is a central component of neuronal toxicity after ischemia.

Example 2—PGG is an Antagonist of CXCR2 Receptor

This Example shows, among other things, that administration of ac-PGG peptide results in effects antagonistic to those of effects of ac-PGP mediated by the CXCR2 receptor.

Primary Cortical Neuron Culture

Cortical neurons were obtained from Sprague-Dawley rat embryos at day 18 of gestation. Cortices were triturated digested with 0.025% trypsin in phosphate buffer saline (PBS) for 10 minutes. Digestion was stopped by the addition of Dulbecco's Modified Eagle Medium (DMEM) containing 10% fetal bovine serum (FBS). Trypsinized cells were filtered using 70 μM disposable cell filters (Becton-Dickinson), washed twice with Neurobasal medium (Gibco) containing 4% FBS, and preplated 4 times for 30 minutes in 150 mm vacuum-plasma treated dishes (Becton-Dickinson). During these re Latin steps, primarily non-neuronal cells adhere to the dish, thereby enriching the neuronal population. Enriched neurons were plated at a density of 50×103/cm2 in Neurobasal medium containing 4% FBS, 25 μM Glutamax (Gibco), and penicillin-streptomycin (Gibco) in white clear-bottomed 96-well plates (353377) or 24-well plates (353226) (Becton-Dickinson) coated overnight with 50 μg/ml poly-D-lysine. At plating, spaces between wells in 96-well plates were filled with 50 μl sterile water to minimize evaporation of medium at the edges of the dish. Twenty-four hours later (1 day in vitro, 1 DIV), 50% of the medium was replaced with Neurobasal medium, 2% B27 (Gibco), and 4 μM cytosine arabinoside (AraC) (2 μM AraC final). At 5 DIV, 50% of the medium was replaced with Neurobasal, 2% B27. At 7 DIV, cortical cultures were 98% neurons as assessed by microtubule-associated protein 2 (MAP2) antibody labeling and flow cytometry analysis (data not shown).

Oxygen-Glucose Deprivation (OGD)

Cortical neurons were deprived of oxygen and glucose by incubation in deoxygenated glucose-free Hank's buffered saline solution (HBSS). HBSS was prepared as follows: sodium chloride, NaCl, 8.0 g/L, potassium chloride, KCl, 0.4 g/L, potassium phosphate monobasic, KH2PO4, 0.06 g/L, sodium phosphate dibasic, Na2HPO4, 0.048 g/L, magnesium sulfate, MgSO4, 0.098 g/L, calcium chloride, CaCl2, 0.14 g/L, sodium bicarbonate, NaHCO3, 0.35 g/L, D-glucose, C6H12O6, 1.0 g/L. Solutions were adjusted to pH 7.4 and sterilized by vacuum filtration through 0.2 μm polyether sulfone (PES) membranes. Glucose-free HBSS was prepared by omitting glucose and adding an additional half molar amount of NaCl to adjust osmolarity (8.162 g/L NaCl). Glucose-free HBSS was deoxygenated in a gas washing bottle with 95% nitrogen, 5% CO2 for 20 minutes at a flow rate of 3 L/min in a 37° C. water bath. Culture dishes were washed twice with deoxygenated glucose-free HBSS and incubated for 2 hours in glucose-free deoxygenated HBSS (OGD). Normoxic control cells were handled identically but were incubated in a 5% CO2 incubator with normal HBSS pre-equilibrated in a 5% CO2 atmosphere overnight.

Results

Figure 3:
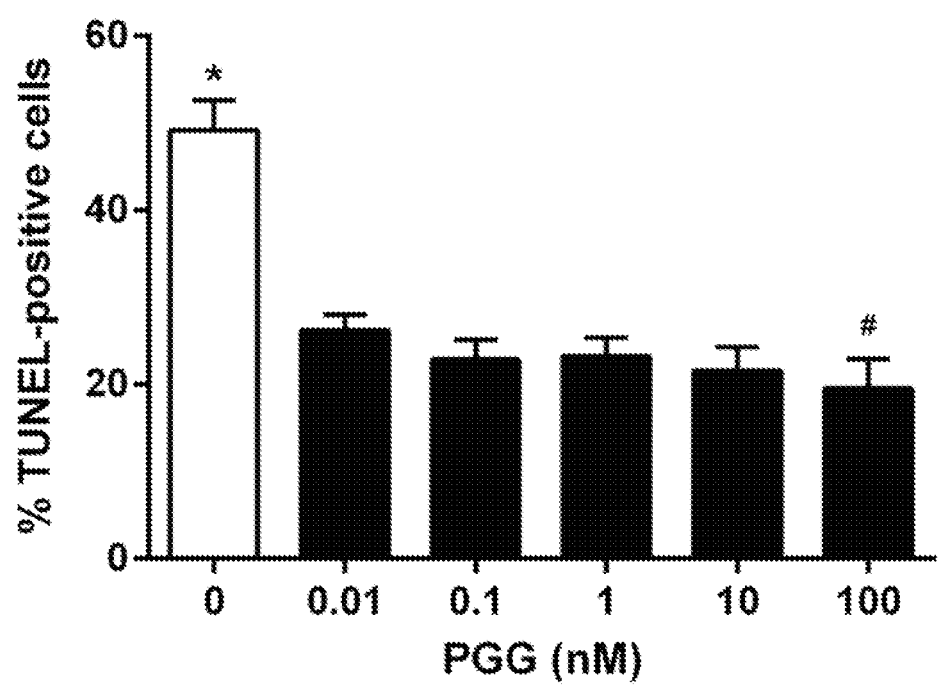
FIG. 3 depicts an exemplary graph showing the effects of pretreatment of neurons with PGG on ac-PGP-induced apoptosis as measured via TUNEL stain. Neurons pretreated with all doses of PGG were significantly less apoptotic than ac-PGP treatment alone (*). Cells pretreated with 100 nM PGG were significantly less apoptotic than cells pretreated with 0.01 nM PGG (#).

It was found that pretreatment of neurons with PGG (FIG. 3) resulted in significant neuroprotection against ac-PGP exposure similar to that observed with established CXCR2 antagonists. These results indicate, that PGG is a potent CXCR2 antagonist when present in concentrations as much as 1000 times below the concentration of a CXCR2 ligand.

Example 2—Neuroprotective Effect of Ac-PGG on Ac-PGP-Induced Apoptosis

This Example shows, among other things, that administration of an ac-PGG peptide results in neuroprotective effects via the CXCR2 receptor.

Figure 4A:
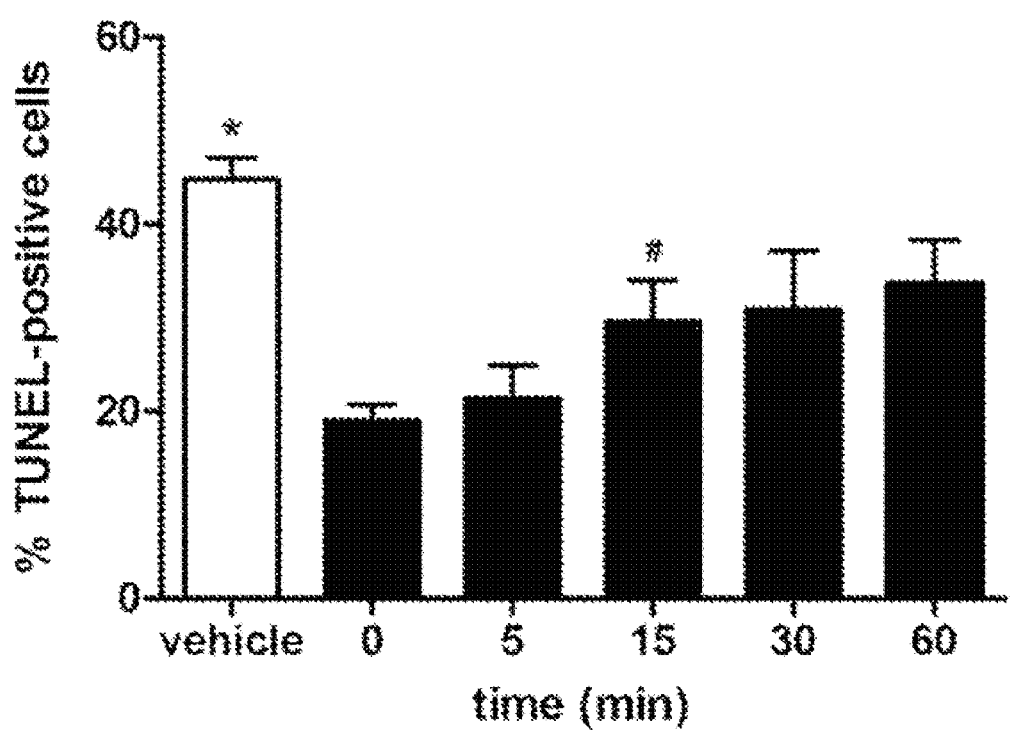
FIG. 4 depicts exemplary graphs showing the effects of treatment with vehicle, SB225002, CXCR2 antibody, or ac-PGG on neurons at reoxygenation or 5, 15, 30, or 60 minutes after reoxygenation in an OGD paradigm. A. Treatment with SB225002 resulted in significant protection from OGD at all time points compared to vehicle (*). When administered at 15 minutes post-reoxygenation, neuronal protection by SB225002 significantly decreased compared to administration at reoxygenation (#). B. Treatment with CXCR2 antibody resulted in significant protection from OGD at all time points compared to vehicle (*). When administered at 60 minutes post-reoxygenation, neuronal protection by CXCR2 antibody significantly decreased compared to administration at reoxygenation (#). C. Treatment with ac-PGG resulted in significant protection from OGD at all time points compared to vehicle (*). No change in the efficacy of neuronal protection by ac-PGG was observed when administered up to 60 minutes after reoxygenation.
Figure 4B:
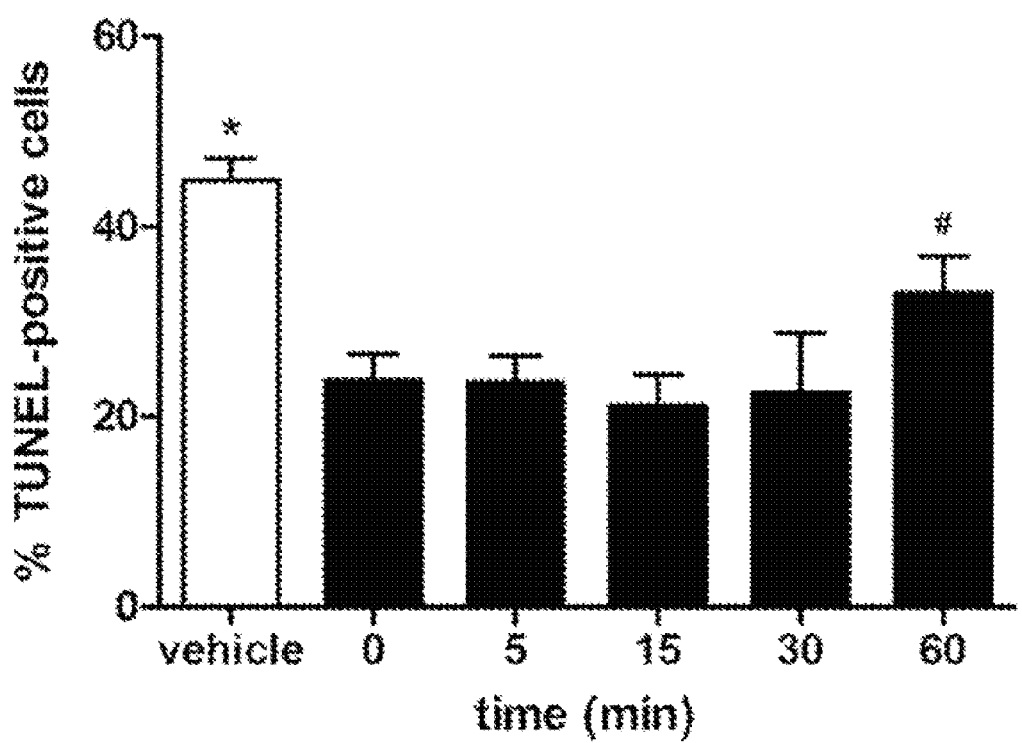
Figure 4C:
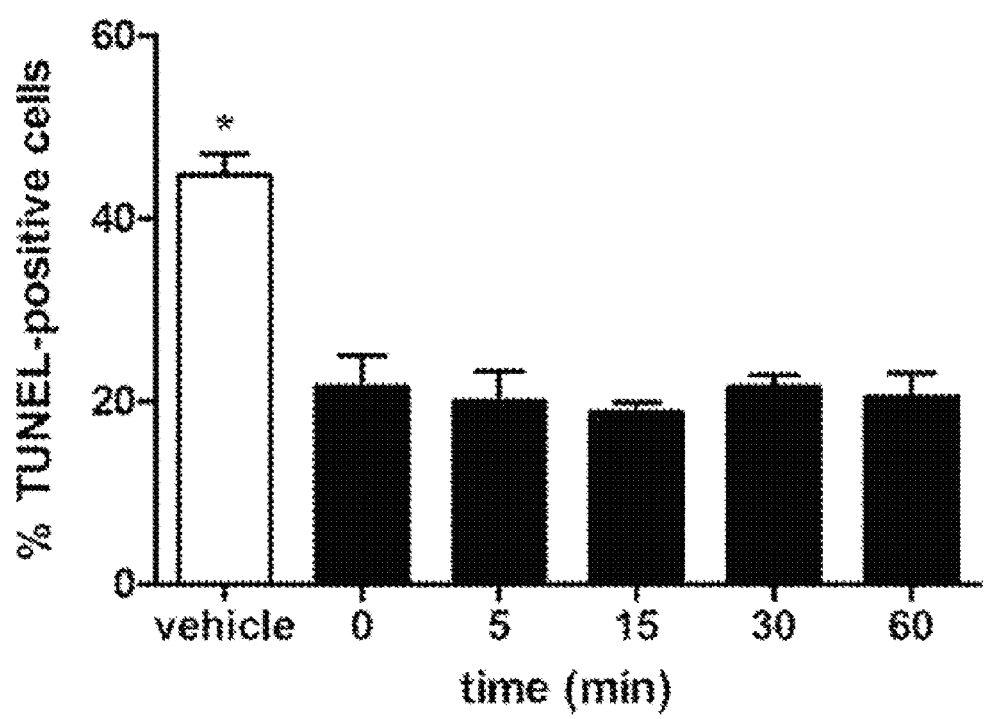

The efficacy of CXCR2 antagonist to prevent neuronal death when given at reoxygenation or at time points up to an hour after reoxygenation was tested (FIG. 4A-C). Primary cortical neuron culture and oxygen-glucose deprivation (OGD) methods, as described above in Example 1, were used to produce the results in this example. As shown in FIG. 4A-C, each of SB2225002, a CXCR2 antibody, and ac-PGG provided neuroprotection when given at reoxygenation and at later time points up to 60 minutes post-reoxygenation. However, the effectiveness of SB225002 significantly declined at 15 minutes post-reoxygenation (FIG. 4A) and the CXCR2 antibody was significantly less protective at 60 minutes post-reoxygenation (FIG. 4B). Ac-PGG treatment was equally as effective at each time point measured (FIG. 4C). These results indicate that ac-PGG is an effective CXCR2 antagonist and neuroprotectant throughout an extended time window after ischemia.

Example 3—Neuroprotective Effect of Ac-PGG in Model of Stroke

This Example shows, among other things, that administration of an ac-PGG peptide results in neuroprotective effects in a model of stroke.

Ac-PGG Formulation and Administration

At reperfusion, animals received 0.5 mL of normal saline vehicle or 0.3, 3, or 30 mg ac-PGG (1, 10, or 100 mg/kg, respectively) in 0.5 mL normal saline by IV injection through the lateral tail vein.

Stroke Model with Spontaneously Hypertensive Rats (SHR)

Male spontaneously hypertensive rats (SHR) weighing 290-300 g were obtained from Charles River Laboratories. Animals were anesthetized with 2% isoflurane inhalant during all surgical procedures. The right common carotid artery (CCA) was ligated approximately 6 mm caudal to the bifurcation of the external and internal carotid arteries. With a vascular clamp in place on the CCA immediately caudal to the bifurcation, an incision was made in the CCA with a 25 G needle 5 mm caudal to the clamp and a 4-0 nylon suture (Doccol Corporation) 30 mm in length with a 2-3 mm silicone coated tip (0.39 mm diameter) was advanced into the CCA lumen and secured in place with 2 4-0 silk sutures spaced 3 mm apart and tied around the CCA caudal to the clamp. The clamp was removed and the suture advanced into the internal carotid artery until resistance was felt. In this position, the filament occluded the middle cerebral artery (MCA) origin and MCA territory became ischemic. The suture was secured with the 2 silk sutures around the CCA. The wound was closed and the animal was allowed to recover during the 90-minute occlusion period. After 90 minutes, the suture was removed and the CCA ligated rostral to the incision.

All animals received 3 mL of subcutaneous saline after surgery to prevent dehydration. After 24 hours reperfusion, brains were sectioned into 4 mm-thick quadrants, and infarcted tissue identified by 2,3,5-triphenyl-tetrazolium chloride (TTC) staining. Edema-corrected infarct volume was calculated by subtracting the area of non-infarcted tissue in the ipsilateral hemisphere from the total volume of the contralateral hemisphere. Infarct volume was quantified using Image J software.

Results

Figure 5:
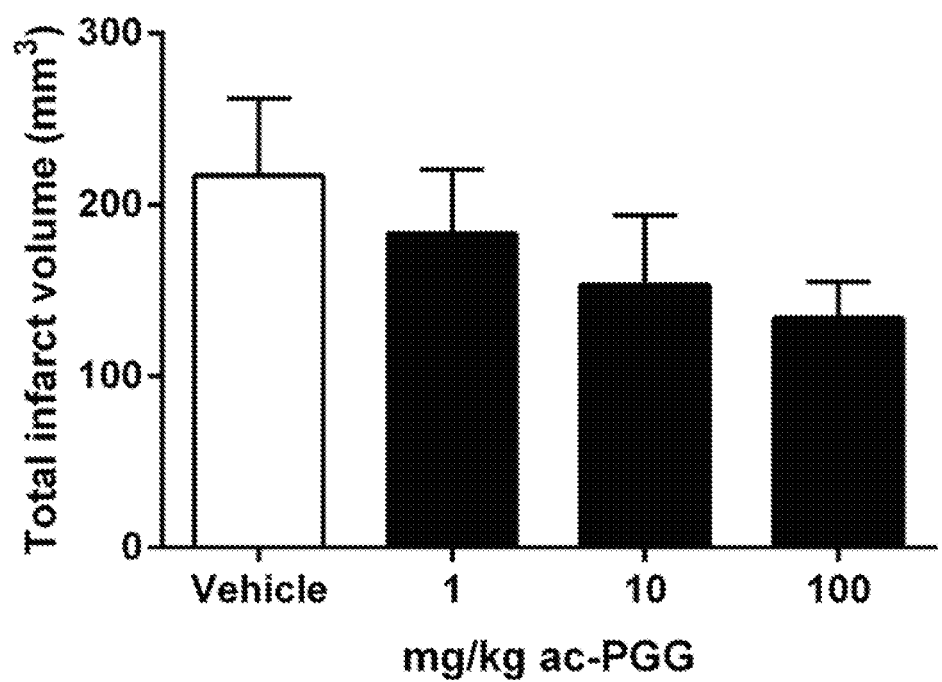
FIG. 5 depicts an exemplary graph showing the effects of treatment with 1, 10 and 100 mg/kg doses of ac-PGG on total infarct volume in a stroke model with Spontaneously Hypertensive Rats (SHR). Treatment with ac-PGG decreased total infarct volume when administered at reperfusion.
Figure 6:
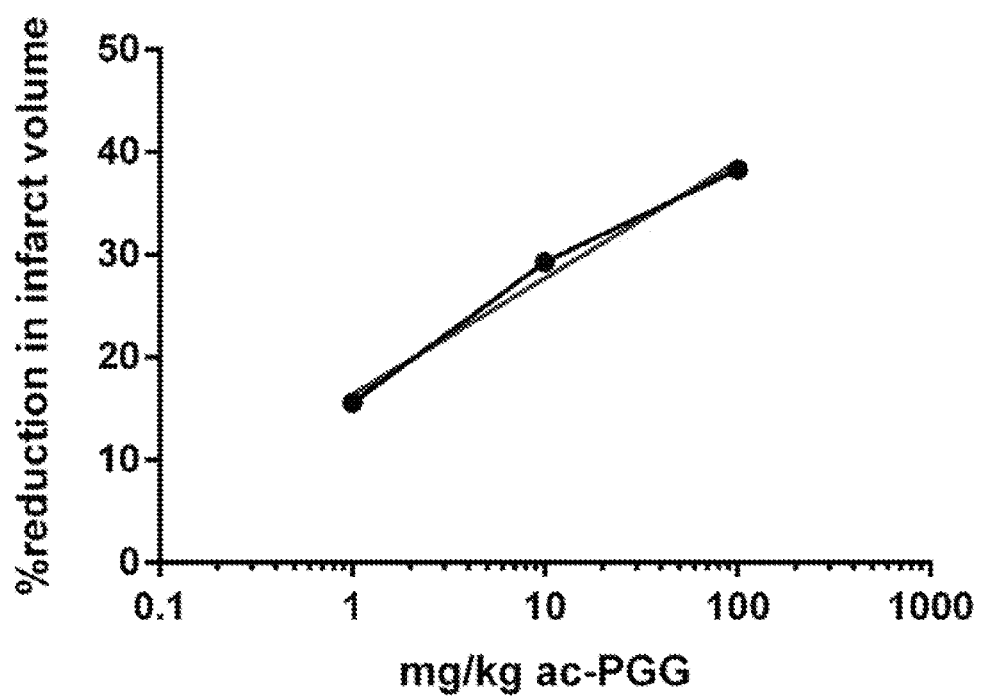
FIG. 6 depicts an exemplary graph showing the effects of treatment with 1, 10 and 100 mg/kg doses of ac-PGG on percent reduction in infarct volume in a stroke model with Spontaneously Hypertensive Rats (SHR). Treatment with ac-PGG increased percent reduction in infarct volume when administered at reperfusion.
Figure 7:
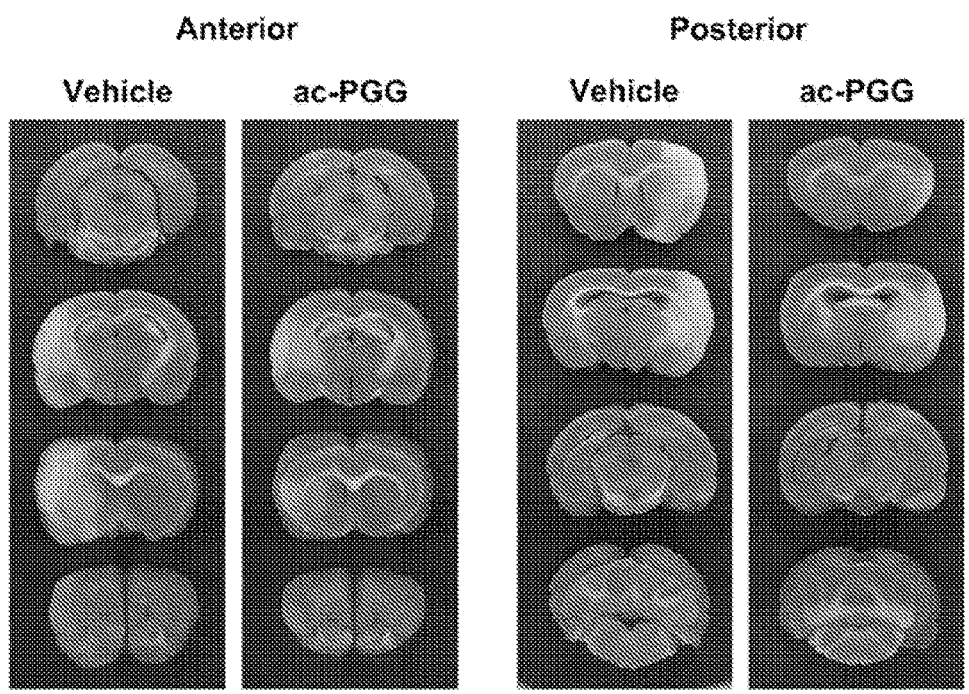
FIG. 7 depicts representative TCC-stained brain sections showing differences in infarction between animals receiving vehicle or 100 mg/kg ac-PGG.

As shown in FIG. 5, treatment with ac-PGG at the time of reperfusion significantly decreased total infarct volume compared to treatment with Vehicle. Additionally, as shown in FIG. 6, treatment with ac-PGG at the time of reperfusion significantly increased the percent reduction in infarct volume. FIG. 7, shows representative TTC-stained brain sections demonstrating differences in infarction between animals receiving vehicle or 100 mg/kg ac-PGG. These results indicate that treatment with ac-PGG can be effective in a stroke model after ischemia, which has clinical relevance due to the real-world necessity to administer treatment hours to days after a stroke.

Example 4—Anti-Inflammatory Effect of Ac-PGG on Carrageenan-Induced Paw Edema

This Example shows, among other things, that administration of ac-PGG peptide results in decreased paw volume and increased latency to response in hot plate test.

Ac-PGG Formulation

Ac-PGG dose volume was 2 mL/kg for IV injections. Ac-PGG was freshly dissolved in saline to a concentration of 200 mg/mL (stock solution) and the working solution of Ac-PGG was diluted in saline at a concentration of 20 mg/mL, 2 mg/mL and 0.2 mg/mL for dose levels of 100 mg/kg, 10 mg/kg, 1 mg/kg and 0.1 mg/kg, respectively.

Carrageenan-Induced Edema

On Day 1, a 1% W/N solution of λ-Carrageenan in saline (0.9% NaCl) was prepared. All animals were lightly anesthetized with isoflurane. A baseline measurement of left hind paw volume for each animal was performed before Carrageenan injection occurred. 100 μL of 1% Carrageenan solution was injected subcutaneously (s.c.) into the planter pad of the left hind paw using a microsyringe.

Paw Volume Measurements

Volumes of the paw injected with Carrageenan were measured with calipers just prior to Carrageenan administration (time 0) and then measured again 1, 3, 4, and 5 hours after Carrageenan injection. Paws were measured in two axes and then paw volume was calculated.

Paw edema volume in this model is an indication of inflammation severity. For each time point, change in paw volume was calculated either by subtracting the baseline paw volume or by determining the % of baseline paw volume.

Hot Plate Test Measurements

One hour before and 3 and 5 hours post-Carrageenan injection, the rats were transported to a testing room and left undisturbed for at least 15 minutes before the test. Illumination in the testing room was 100-130 Lux at the level of the bench (red light). The hot plate was maintained thermostatically at a temperature of 50° C. One rat at a time was placed on the hot plate platform and latency to jumping or lifting the Carrageenan-injected paw or the control paw was recorded. The latency of the response was measured in a blinded manner. In the absence of a response, a 30 second cut-off was used to prevent tissue damage.

Ac-PGG Administration

Ac-PGG was administered by a single intravenous (IV) injection half an hour before Carrageenan injection. See Table 1 for group allocations.

TABLE 1

| Group | Treatment | Dose | Administration | Total rats |
| --- | --- | --- | --- | --- |
| 1 | Vehicle | 0 | IV | 7 |
| 2 | Ac-PGG | 0.1 mg/kg | IV | 7 |
| 3 | Ac-PGG | 1 mg/kg | IV | 7 |
| 4 | Ac-PGG | 10 mg/kg | IV | 7 |

TABLE 1-continued

| Group | Treatment | Dose | Administration | Total rats |
|---|---|---|---|---|
| 5 | Ac-PGG | 100 mg/kg | IV | 7 |
| 6 | Indomethacin | 2 mg/kg | IP | 7 |

Results

Figure 8:
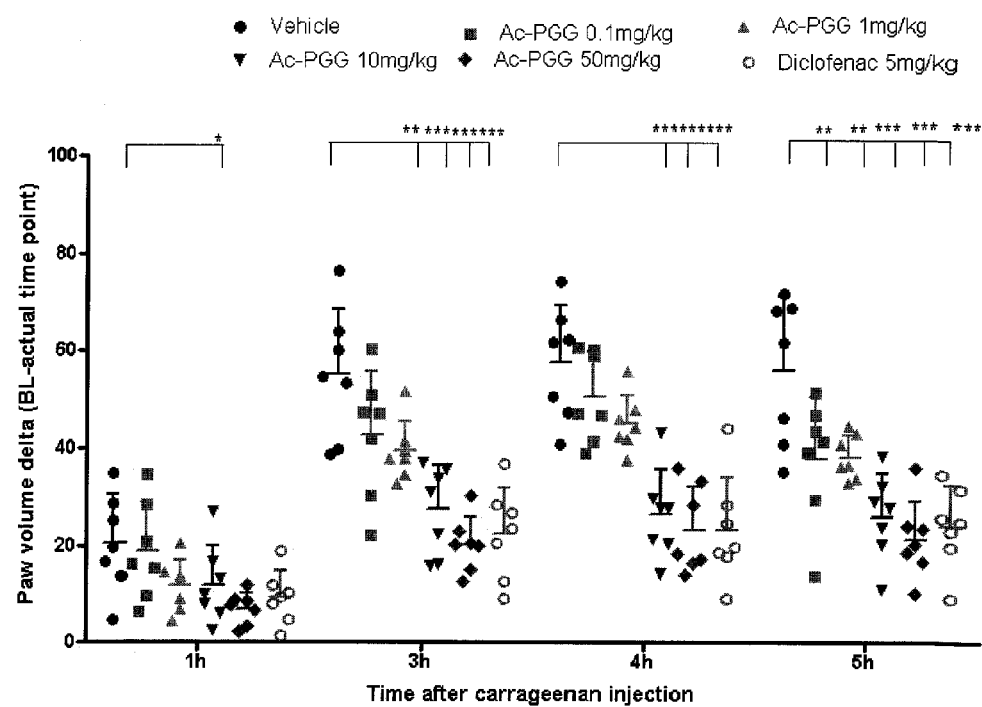
FIG. 8 depicts an exemplary graph showing the effects of 0.1, 10, 1, and 50 mg/kg doses of ac-PGG on a Carrageenan-induced change in paw volume. The 3 highest doses of ac-PGG decreased the Carrageenan-induced increase in paw volume at 3, 4, and 5 hours post-Carrageenan injection.

The 3 highest doses of ac-PGG decreased the Carrageenan-induced increase in paw volume. As shown in FIG. 8, the 3 highest doses of ac-PGG decreased the Carrageenan-induced increase in paw volume at 3, 4, and 5 hours post-Carrageenan injection. Additionally, the 50 mg/kg dose of ac-PGG significantly decreased the change in paw volume compared to the Vehicle group after 1 hour. Also, even the 0.1 mg/kg dose of ac-PGG significantly decreased the change in paw volume 5 hours post-Carrageenan injection.

Figure 9:
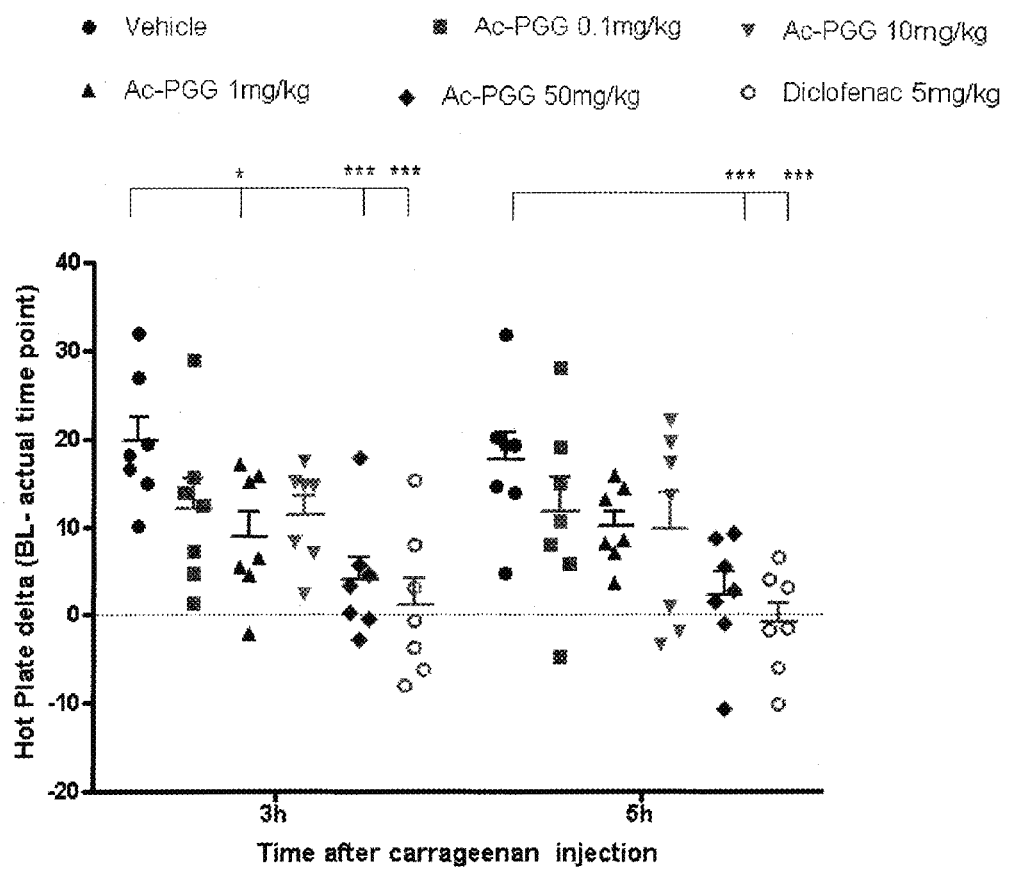
FIG. 9 depicts an exemplary graph showing the effects of 0.1, 10, 1, and 50 mg/kg doses of ac-PGG on latency to respond to a hot plate. The 1 mg/kg and 50 mg/kg doses of ac-PGG decreased change in latency to hot plate response 3 hours after Carrageenan injection, while only the 50 mg/kg dose lead to a significant decrease in latency change 5 hours after Carrageenan injection.

Treatment with ac-PGG significantly increased latency to respond to the hot plate. As shown in FIG. 9, the 1 mg/kg and 50 mg/kg doses of ac-PGG decreased change in latency to hot plate response 3 hours after Carrageenan injection, while only the 50 mg/kg dose lead to a significant decrease in latency change 5 hours after Carrageenan injection.

Example 5—Anti-Inflammatory Effect of Ac-PGG on EAE-Induced Paralysis

This Example shows, among other things, that administration of ac-PGG peptide results in decreased paralysis and weight loss in an experimental autoimmune encephalomyelitis (EAE) model.

Ac-PGG Formulation

Ac-PGG dose was 100 mg/kg for subcutaneous injections. Treatment animals received 30 mg ac-PGG in 200 μL normal saline.

EAE Induction

Male Lewis rats (10 weeks old) were obtained from Charles River Laboratories. After a 1-week acclimation period, EAE was induced by injecting animals subcutaneously at the base of the tail with 100 μg guinea pig myelin basic protein in 50 μL normal Saline mixed with 150 μL Freund's complete adjuvant for a 200 μL total injection volume.

EAE Scoring

Animals were weighed and assigned an EAE score daily for 25 days. The criteria used for EAE scoring are presented in Table 2.

TABLE 2

| Score | Sign |
|---|---|
| 0 | Normal |
| 1 | Weak distal tail |
| 2 | Weak proximal tail |
| 3 | Tail paralysis |
| 4 | Tail paralysis and hindlimb weakness |
| 5 | Partial hindlimb paralysis (one limb) |
| 6 | Hindlimb paralysis |
| 7 | Hindlimb paralysis and forelimb weakness |
| 8 | Hindlimb paralysis, forelimb weakness, and side resting position |
| 9 | Hindlimb paralysis, forelimb paralysis, and side resting position |
| 10 | Hindlimb paralysis, forelimb paralysis, and unresponsive to stimuli |

Ac-PGG Administration

Ac-PGG was administered by subcutaneous injection on the hindquarters starting with the left hindquarter and alternating sides with each injection. Treatment animals received ac-PGG on days 0-7 or 8-15 and received 200 μL subcutaneous injections of saline on days when ac-PGG was not administered. Vehicle animals were administered 200 μL normal saline on days 0-15 by subcutaneous injection on the hindquarters starting with the left hindquarter and alternating sides with each injection.

Results

Figure 10:
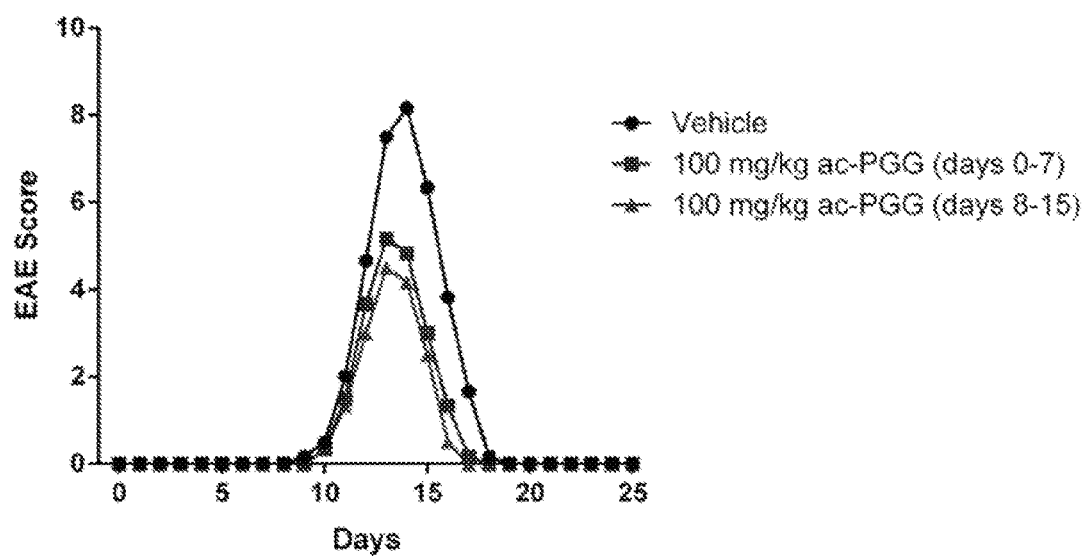
FIG. 10 depicts an exemplary graph showing the effects of two dosing schedules of ac-PGG on EAE score. Both ac-PGG dosing schedules decreased EAE scores compared to the Vehicle group.
Figure 11:
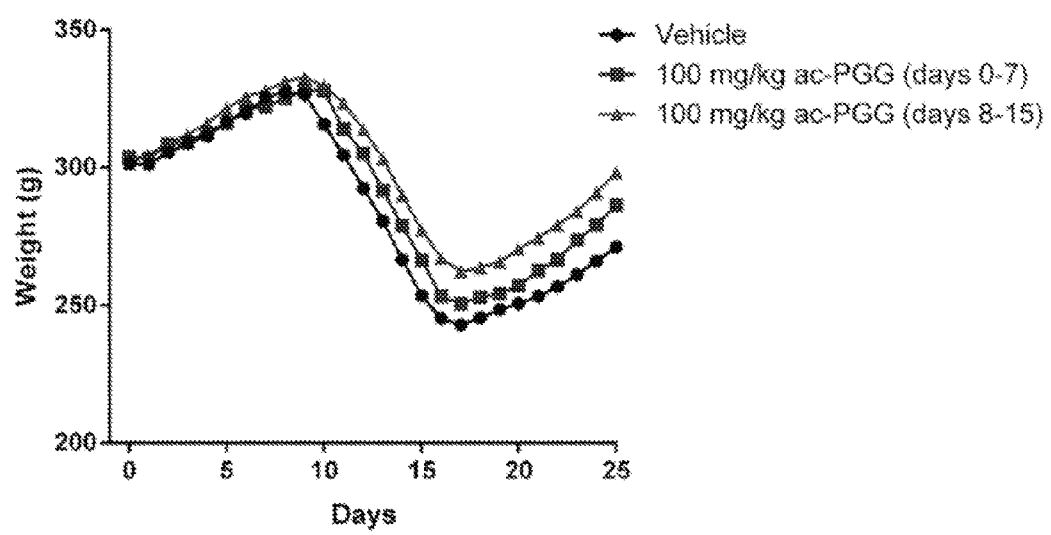
FIG. 11 depicts an exemplary graph showing the effects of two dosing schedules of ac-PGG on weight. Both ac-PGG dosing schedules increased weight compared to the Vehicle group over the course of the study.

Both ac-PGG dosing schedules (days 0-7 and days 8-15) decreased the EAE-induced paralysis. As shown in FIG. 10, both ac-PGG dosing schedules significantly decreased both EAE scores pooled over 26 days and Day 14 EAE scores. Additionally, as shown in FIG. 11, both ac-PGG dosing schedules significantly increased weight compared to the Vehicle group over the course of the study and there was a significant difference between the final weights of the Vehicle group and the ac-PGG (days 8-15) group on Day 25.

Figure 12:
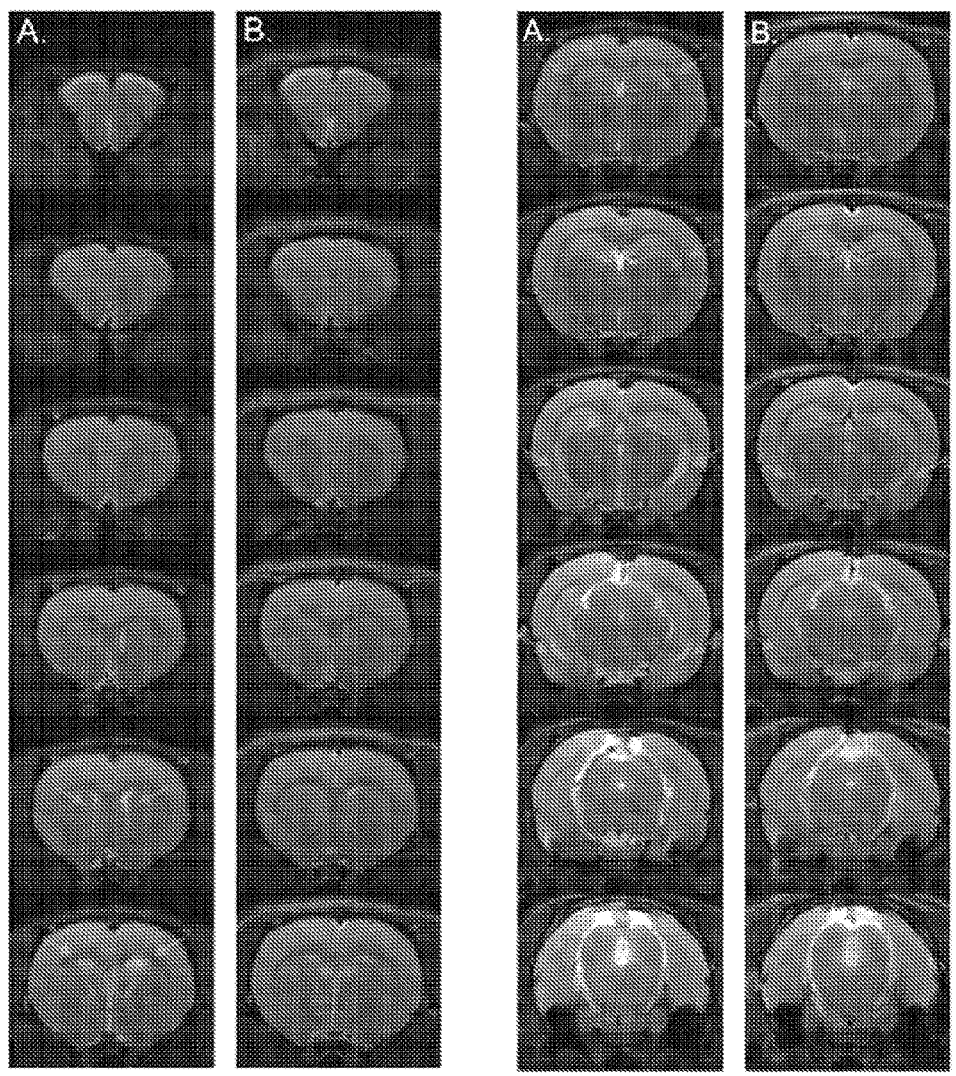
FIG. 12 depicts exemplary MRI pictures from Day 14 of EAE induction showing the effects of treatment with ac-PGG (days 8-15) on white matter hyperintensities. Treatment with ac-PGG decreased the number of white matter hyperintensities seen with T2-weighted MRI scans.

Ac-PGG also decreased white matter hyperintensities as detected by T2-weighted MRI. As shown in FIG. 12, in animals treated with ac-PGG on days 8-15, fewer coronal brain sections contained white matter hyperintensities on Day 14 of EAE induction compared to Vehicle-treated animals.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. A pharmaceutical composition in unit dosage form for administration to a human patient comprising a therapeutically effective amount of at least one compound selected from the group consisting of a tripeptide with the amino acid sequence proline-glycine-glycine (PGG tripeptide), a PGG tripeptide which is acetylated or methylated at its N-terminus, a PGG tripeptide which is amidated at its C-terminus, a PGG tripeptide which is PEGylated, a pharmaceutically acceptable salt thereof, and mixtures thereof, further including an effective amount of at least one anti-inflammatory agent, anticancer agent, neuroprotective agent, thrombolytic agent, immunosuppressant, antioxidant, α- or β-adrenergic agonist or antagonist, or NMDA receptor antagonist, in combination with a pharmaceutically acceptable carrier or excipient.

2. The composition according to claim 1, wherein said compound is the tripeptide with the amino acid sequence proline-glycine glycine (PGG), a pharmaceutically acceptable salt thereof or a mixture thereof.

3. The composition according to claim 1 wherein said compound is the tripeptide which is acetylated or methylated at the N-terminus, a pharmaceutically acceptable salt thereof or a mixture thereof.

4. The composition according to claim 3 wherein said compound is the tripeptide which is acetylated at the N-terminus.

5. A pharmaceutical composition in unit dosage form for administration to a human patient comprising a tripeptide with the amino acid sequence proline-glycine-glycine (PGG) wherein the peptide is acetylated or methylated at the N-terminus, PEGylated, or amidated at the C-terminus in any combination thereof, further including an effective amount of at least one anti-inflammatory agent, anticancer agent, neuroprotective agent, thrombolytic agent, immunosuppressant, antioxidant, α- or β-adrenergic agonist or antagonist, or NMDA receptor antagonist, in combination with a pharmaceutically acceptable carrier or excipient.

6. The pharmaceutical composition of claim 1 which is adapted for intravenous, subcutaneous, oral, transdermal, aerosol inhalation, intramuscular, or intraperitoneal administration.

7. The pharmaceutical composition of claim 5 which is adapted for intravenous, subcutaneous, oral, transdermal, aerosol inhalation, intramuscular, or intraperitoneal administration.

\* \* \* \* \*